US008501778B2

United States Patent
Li et al.

(10) Patent No.: US 8,501,778 B2
(45) Date of Patent: Aug. 6, 2013

(54) ARALKYL PIPERIDINE DERIVATIVES AND THEIR USES AS ANTALGIC OR ATARACTIC AGENT

(75) Inventors: Jianqi Li, Shanghai (CN); Guan Wang, Shanghai (CN); Guisen Zhang, Xuzhou (CN); Yanqin Ma, Xuzhou (CN); Wenhua Ji, Shanghai (CN); Yuan Zhang, Shanghai (CN); Lin Guo, Xuzhou (CN)

(73) Assignees: NHWA Pharma. Corporation, Xuzhou, Jiangsu (CN); Shanghai Institute of Pharmaceutical Industry, Shanghai (CN)

( * ) Notice: Subject to any disclaimer, the term of this patent is extended or adjusted under 35 U.S.C. 154(b) by 171 days.

(21) Appl. No.: 13/000,066

(22) PCT Filed: Jun. 20, 2008

(86) PCT No.: PCT/CN2008/001206
§ 371 (c)(1),
(2), (4) Date: Dec. 20, 2010

(87) PCT Pub. No.: WO2009/152647
PCT Pub. Date: Dec. 23, 2009

(65) Prior Publication Data
US 2011/0105503 A1  May 5, 2011

(51) Int. Cl.
*A61K 31/445* (2006.01)
*C07D 211/48* (2006.01)

(52) U.S. Cl.
USPC ........... 514/317; 514/327; 546/216; 546/221; 546/239; 546/240; 546/241

(58) Field of Classification Search
USPC ................ 514/317, 327; 546/216, 221, 239, 546/240, 241
See application file for complete search history.

(56) References Cited

U.S. PATENT DOCUMENTS

| | | | |
|---|---|---|---|
| 5,583,000 A | | 12/1996 | Ortiz de Montellano et al. |
| 5,610,303 A | * | 3/1997 | Kimura et al. ................. 544/326 |
| 7,332,495 B2 | | 2/2008 | Li et al. |

FOREIGN PATENT DOCUMENTS

| | | |
|---|---|---|
| CN | 1381449 A | 11/2002 |
| CN | 101260075 A | 9/2008 |
| WO | 9118602 A1 | 12/1991 |
| WO | 9734603 A1 | 9/1997 |

OTHER PUBLICATIONS

Wikipedia derivatives p. 1 (2012).*
Kimura et al. "Preparation of . . ." CA121:300912 (1994).*
Seddon "Pseudopolymorph . . ." Crystal Growth & design v.4(6) p. 1087 (2004).*
EP Supplemental Search Report issued Jul. 12, 2011 in EP Application No. 08772968.7.
Palin et al, "Novel Piperidinium and Pyridinium Agents as Water-Soluble Acetylcholinesterase Inhibitors for the Reversal of Neuromuscular Blockade," Bioorganic & Medicinal Chemistry Letters, vol. 12, pp. 2569-2572 (2002).
Int'l Search Report issued Mar. 26, 2009 in Int'l Application No. PCT/CN2008/001206.

* cited by examiner

*Primary Examiner* — Celia Chang
(74) *Attorney, Agent, or Firm* — Panitch Schwarze Belisario & Nadel LLP

(57) ABSTRACT

The present invention relates to aralkyl piperidine derivatives, compositions containing the same, and their uses in the preparation of antalgic or ataractic medicament. The said derivatives are a free base of the compound represented by the following formula or a salt thereof. The pharmacological experiments show that they display favorable antalgic, ataractic activity and low side effects.

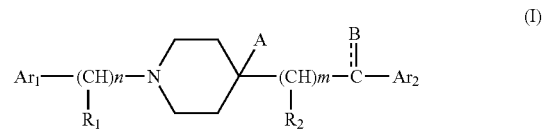

(I)

12 Claims, No Drawings

ARALKYL PIPERIDINE DERIVATIVES AND THEIR USES AS ANTALGIC OR ATARACTIC AGENT

CROSS-REFERENCE TO RELATED APPLICATION

This application is a section 371 of International Application No. PCT/CN2008/001206, filed Jun. 20, 2008, which was published in the Chinese language on Dec. 23, 2009 under International Publication No. WO 2009/152647 A1 and the disclosure of which is incorporated herein by reference.

TECHNICAL FIELD

The present invention relates to an aralkyl piperidine derivative and use thereof in the preparation of an antalgic or ataractic agent.

BACKGROUND

Serious acute and chronic pains are nociception and pains caused by introducing excitement of nociceptor due to various damage stimuli into central nervous system through impulse of transporter of nociceptive information. Serious acute and chronic pains include tumor pain, postoperative pain, and various recurrent acute and chronic pains, which perplex millions of patents, and are a major clinical problem currently.

The use of the existing opioid antalgic agents is limited due to drug addiction and side effects of respiratory depression, gastric motility reduction, etc. Therefore, to find central antalgic drugs that not only maintain a strong antalgic effect but also overcome the above defects and can be clinically applied safely is the main target in the antalgic field and studies on novel drugs. Although tremendous effects have been made on chemical and biological field during the last ten years, not any big progresses are made yet. Studies on novel central antalgic drugs have become the focus of the field. Large pharmaceutical companies such as Pfizer and Merck have invested huge capitals in the development of a novel non-addictive central antalgic agent.

Currently used non-opioid antalgics mainly include, based on the action mechanisms, NMDA receptor antagonist (such as ketamine), 5-HT reuptake inhibitor (such as tramadol), potassium channel opener (such as flupirtine), cyclooxygenase 2 inhibitors (such as celecoxib), calcium channel antagonist (such as Ziconotide), etc. These drugs improve the drug addiction and side effects compared with previous drugs to some extent, as specifically introduced in, for example, U.S. Pat. No. 6,339,105, U.S. Pat. No. 4,481,205, U.S. Pat. No. 5,760,068, U.S. Pat. No. 5,189,020, yet still have different degree of drug addiction or large toxic side effects. For example, ketamine, tramadol and flupirtine still cause addiction; celecoxib has potential side effects one cardiovascular; ziconotide may cause orthostatic hypotension easily, etc. In addition, effects of currently existing drugs are far from the requirements of control of pain of different clinical patients, in particular for some cancer pain, serious chronic pain and some neuropathic pain. There are no appropriate, safe and effective antalgic drugs. Therefore, there is a continuous need to develop non-addictive antalgic drugs having novel chemical structure, less toxic side effect, and being widely applicable and clinically safe to meet requirements of different patients suffering from pains. Further, market demand for non-opioid antalgic drugs is tremendous. A novel antalgic drug will generate great social and economic benefits.

The present inventor discloses an aralkyl-ketone piperazine derivative and use of the derivative as a novel antalgic and sedative drug in the application for Chinese patent for invention of the No. CN1381449 in 2002, wherein the compound has a non-addictive central antalgic effect. The aralkyl piperidine derivative of the present invention is a novel compound not disclosed, which has different chemical structure, even less toxic side effects and higher safety compared with the above application for patent.

THE CONTENT OF THE INVENTION

One of the problems to be solved by the present invention is to disclose a type of aralkyl piperidine derivative compounds that are pharmaceutically useful for overcoming the defects of causing drug addiction and the side effects of respiratory depression and gastric motility reduction, solving clinical problems, and meeting people's requirements to antalgic.

The second problem to be solved by the present invention is to disclose use of the above compounds as a novel antalgic or sedative medicament.

The aralkyl piperidine derivative of the present invention is a free base of the compound represented by the following formula or a salt thereof, the salt is hydrochloride, hydrobromide, sulfate, trifluoroacetate or methylsulfonate, etc., preferably the salt is hydrochloride, hydrobromide, wherein the salt contains 0.5-3 molecules of crystal waters:

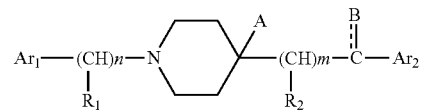

wherein:

A represents: OH, F, Cl, Br, $(C_1-C_4)$alkoxy, wherein alkyl moiety of $(C_1-C_4)$alkoxy may be substituted optionally by 1-3 fluorine atom(s) and further substituted optionally by amino or hydroxy substituents;

When B is connected with an adjacent carbon through a single bond, B represents OH;

When B is connected with an adjacent carbon through a double bond, B represents O or S;

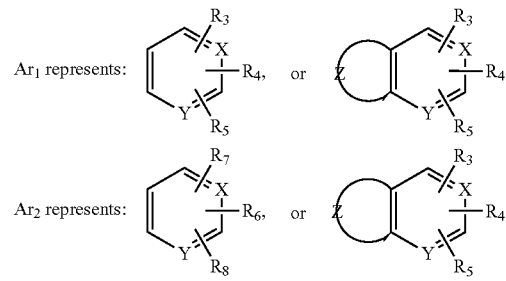

X and Y each independently represent C, CH or N;

Z represents a five- or six-membered saturated or unsaturated aliphatic heterocycle or aromatic heterocycle containing N, O, S heteroatoms, wherein the total number of the heteroatoms is less than or equals to 3;

$R_1$ and $R_2$ each independently represent one of hydrogen, $C_1-C_4$ alkyl, a $C_5$ or $C_6$ aliphatic ring, phenyl and substituted phenyl, hydroxy, $(C_1-C_4)$alkoxy, amino and substituted amino, halogen, carboxyl and carboxylic ester, nitro or acetonitrile, wherein the alkyl moiety in the $C_1$-$C_4$ alkyl, ($C_1$-$C_4$) alkoxy and $C_5$ or $C_6$ aliphatic ring may be substituted optionally by 1-3 fluorine atom(s) and further substituted optionally by amino or hydroxy substituents;

$R_3$, $R_4$ and $R_5$ each independently represent one of hydrogen, $C_1$-$C_4$ alkyl, a $C_5$ or $C_6$ aliphatic ring, a five- or six-membered saturated or unsaturated aliphatic ring containing one or two N, O, S heteroatoms, phenyl and substituted phenyl, hydroxy, ($C_1$-$C_4$)alkoxy, amino and substituted amino, halogen, carboxyl and carboxylic ester, nitro or acetonitrile, wherein the alkyl moiety in the $C_1$-$C_4$ alkyl, ($C_1$-$C_4$)alkoxy and $C_5$ or $C_6$ aliphatic ring may be substituted optionally by 1-3 fluorine atom(s) and further substituted optionally by amino or hydroxy substituents;

$R_6$, $R_7$ and $R_8$ each independently represent one of hydrogen, $C_1$-$C_4$ alkyl, a $C_5$ or $C_6$ aliphatic ring, a five- or six-membered saturated or unsaturated aliphatic ring containing one or two N, O, S heteroatoms, phenyl and substituted phenyl, hydroxy, ($C_1$-$C_4$)alkoxy, halogen, carboxyl and carboxylic ester, nitro or acetonitrile, wherein the alkyl moiety in the $C_1$-$C_4$ alkyl, ($C_1$-$C_4$)alkoxy and $C_5$ or $C_6$ aliphatic ring may be substituted optionally by 1-3 fluorine atom(s) and further substituted optionally by amino or hydroxy substituents;

n=0, 1, 2, 3; m=1, 2, 3; when n, m=2, 3, substituents $R_1$ and $R_2$ can be connected directly with any one or more carbon(s) on a carbon chain.

Preferably A is one of OH, F or Cl.

Preferably $R_1$, $R_2$ are one of hydrogen, $C_1$-$C_4$ alkyl or phenyl and substitute phenyl.

Preferably $R_3$, $R_4$, $R_5$ are one of hydrogen, $C_1$-$C_4$ alkyl, hydroxy, methoxy, ethoxy, amino and substituted amino, morpholino, pyrrolidinyl, piperidinyl, halo or nitro.

Preferably $R_6$, $R_7$, $R_8$ are one of hydrogen, $C_1$-$C_4$ alkyl, hydroxy, methoxy, ethoxy, halo, morpholino, pyrrolidinyl or piperidinyl.

The preferable compounds include:

III-1 N-benzyl-4-benzoylmethyl-4-piperidinol
III-2 N-p-chlorobenzyl-4-benzoylmethyl-4-piperidinol
III-3 N-p-fluorobenzyl-4-benzoylmethyl-4-piperidinol
III-4 N-p-nitrobenzyl-4-benzoylmethyl-4-piperidinol
III-5 N-p-aminobenzyl-4-benzoylmethyl-4-piperidinol
III-6 N-p-acetylaminobenzyl-4-benzoylmethyl-4-piperidinol
III-7 N-diphenylmethyl-4-benzoylmethyl-4-piperidinol
III-8 N-(2-pyridyl)methyl-4-benzoylmethyl-4-piperidinol
III-9 N-(2-pyrimidinyl)-4-benzoylmethyl-4-piperidinol
III-10 N-(2-pyrimidinyl)methyl-4-benzoylmethyl-4-piperidinol
III-11 N-(2-quinolyl)-4-benzoylmethyl-4-piperidinol
III-12 N-(2-methoxyphenyl)-4-benzoylmethyl-4-piperidinol
III-13 N-(benzo[d][1,3]dioxol-5-ylmethyl)-4-benzoylmethyl-4-piperidinol
III-14 N-(3,4,5-trimethoxybenzyl)-4-benzoylmethyl-4-piperidinol
III-15 N-p-methoxybenzyl-4-benzoylmethyl-4-piperidinol
III-16 N-(1-phenylethyl)-4-benzoylmethyl-4-piperidinol
III-17 (R)—N-(1-phenylethyl)-4-benzoylmethyl-4-piperidinol
III-18 (S)—N-(1-phenylethyl)-4-benzoylmethyl-4-piperidinol
III-19 N-(1-(4-methoxyphenyl)ethyl)-4-benzoylmethyl-4-piperidinol
III-20 N-(1-(4-fluorophenyl)ethyl)-4-benzoylmethyl-4-piperidinol
III-21 N-(1-(4-aminophenyl)ethyl)-4-benzoylmethyl-4-piperidinol
III-22 N-(1-(benzo[d][1,3]dioxol-5-yl)ethyl)-4-benzoylmethyl-4-piperidinol
III-23 N-(2-naphthylmethyl)-4-benzoylmethyl-4-piperidinol
III-24 N-(4-(1-pyrrolidinyl)benzyl)-4-benzoylmethyl-4-piperidinol
III-25 N-(1-(4-(1-pyrrolidinyl)phenyl)ethyl)-4-benzoylmethyl-4-piperidinol
III-26 N-(4-morpholinobenzyl)-4-benzoylmethyl-4-piperidinol
III-27 N-(1-(4-morpholinophenyl)ethyl)-4-benzoylmethyl-4-piperidinol
III-28 N-(4-(1-piperidinyl)benzyl)-4-benzoylmethyl-4-piperidinol
III-29 N-(2-oxo-5-indolinyl)methyl-4-benzoylmethyl-4-piperidinol
III-30 N-(5-indolinyl)methyl-4-benzoylmethyl-4-piperidinol
III-31 N-benzyl-4-(p-fluorobenzoylmethyl)-4-piperidinol
III-32 N-benzyl-4-(p-methoxybenzoylmethyl)-4-piperidinol
III-33 N-benzyl-4-(p-chlorobenzoylmethyl)-4-piperidinol
III-34 N-benzyl-4-(2-pyridinylformylmethyl)-4-piperidinol
III-35 N-benzyl-4-(4-(pyrrolidinyl)benzoylmethyl)-4-piperidinol
III-36 N-benzyl-4-((4-morpholinobenzoyl)methyl)-4-piperidinol
III-37 N-benzyl-4-(2-(5-indolinyl)-2-oxoethyl)-4-piperidinol
III-38 N-benzyl-4-(2-(benzo[d][1,3]dioxol-5-yl)-2-oxoethyl)-4-piperidinol
III-39 N-benzyl-4-(1-benzoylethyl)-4-piperidinol
V-1 N-p-methoxybenzyl-4-(2-hydroxy-2-phenylethyl)-4-piperidinol
V-2 N-p-acetylaminobenzyl-4-(2-hydroxy-2-phenylethyl)-4-piperidinol
V-3 N-diphenylmethyl-4-(2-hydroxy-2-phenylethyl)-4-piperidinol
V-4 N-(benzo[d][1,3]dioxol-5-ylmethyl)-4-(2-hydroxy-2-phenylethyl)-4-piperidinol
V-5 N-(2-methoxyphenyl)-4-(2-hydroxy-2-phenylethyl)-4-piperidinol
V-6 N-(5-indolinyl)methyl-4-(2-hydroxy-2-phenylethyl)-4-piperidinol
V-7 N-(1-(4-(pyrrolidinyl)phenyl)ethyl)-4-(2-hydroxy-2-phenylethyl)-4-piperidinol
V-8 N-(1-(4-morpholinophenyl)ethyl)-4-(2-hydroxy-2-phenylethyl)-4-piperidinol
VIII-1 N-p-acetylaminobenzyl-4-benzoylmethyl-4-methoxylpiperidine
VIII-2 N-(1-(p-methoxyphenyl)ethyl)-4-benzoylmethyl-4-methoxylpiperidine
VIII-3 N-(1-(4-morpholinophenyl)ethyl)-4-benzoylmethyl-4-methoxylpiperidine
IX-1 N-(1-(p-methoxyphenyl)ethyl)-4-benzoylmethyl-4-fluoropiperidine
IX-2 N-(benzo[d][1,3]dioxol-5-ylmethyl)-4-benzoylmethyl-4-fluoropiperidine
IX-3 N-(1-(4-morpholinophenyl)ethyl)-4-benzoylmethyl-4-fluoropiperidine
IX-4 N-(1-(4-(pyrrolidinyl)phenyl)ethyl)-4-benzoylmethyl-4-fluoropiperidine
IX-5 N-(1-(p-methoxyphenyl)ethyl)-4-benzoylmethyl-4-chloropiperidine
IX-6 N-(benzo[d][1,3]dioxol-5-ylmethyl)-4-benzoylmethyl-4-chloropiperidine
IX-7 N-(1-(4-morpholinophenyl)ethyl)-4-benzoylmethyl-4-chloropiperidine The specific chemical structures of the above preferable compounds are shown in Table 1:
TABLE 1
| No. | Ar₁ | Ar₂ | R₁ | R₂ | A | C=B | n | m |
|---|---|---|---|---|---|---|---|---|
| III-1 | Ph | Ph | H | H | OH | C=O | 1 | 1 |
| III-2 | 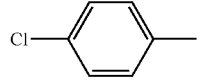 | Ph | H | H | OH | C=O | 1 | 1 |
| III-3 | 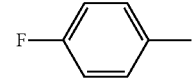 | Ph | H | H | OH | C=O | 1 | 1 |
| III-4 | 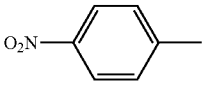 | Ph | H | H | OH | C=O | 1 | 1 |
| III-5 | 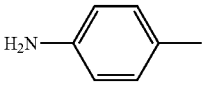 | Ph | H | H | OH | C=O | 1 | 1 |
| III-6 | 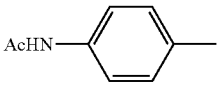 | Ph | H | H | OH | C=O | 1 | 1 |
| III-7 | (Ph)₂CH— | Ph | H | H | OH | C=O | 1 | 1 |
| III-8 | 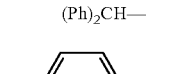 | Ph | H | H | OH | C=O | 1 | 1 |
| III-9 | 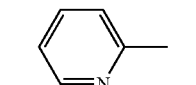 | Ph | H | H | OH | C=O | 0 | 1 |
| III-10 | 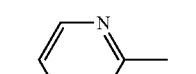 | Ph | H | H | OH | C=O | 1 | 1 |
| III-11 | 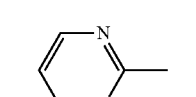 | Ph | H | H | OH | C=O | 0 | 1 |
| III-12 | 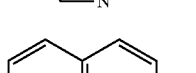 | Ph | H | H | OH | C=O | 0 | 1 |
| III-13 | 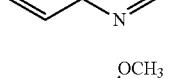 | Ph | H | H | OH | C=O | 1 | 1 |
| III-14 | 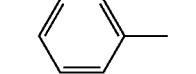 | Ph | H | H | OH | C=O | 1 | 1 |

TABLE 1-continued
| No. | Ar₁ | Ar₂ | R₁ | R₂ | A | C=B | n | m |
|---|---|---|---|---|---|---|---|---|
| III-15 | 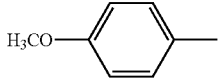 | Ph | H | H | OH | C=O | 1 | 1 |
| III-16* | Ph | Ph | CH₃ | H | OH | C=O | 0 | 1 |
| III-19 | 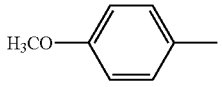 | Ph | CH₃ | H | OH | C=O | 1 | 1 |
| III-20 | 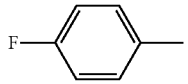 | Ph | CH₃ | H | OH | C=O | 1 | 1 |
| III-21 | 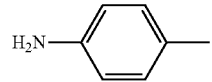 | Ph | CH₃ | H | OH | C=O | 1 | 1 |
| III-22 | 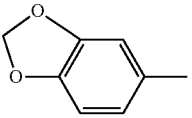 | Ph | CH₃ | H | OH | C=O | 1 | 1 |
| III-23 | 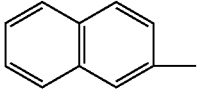 | Ph | H | H | OH | C=O | 1 | 1 |
| III-24 | 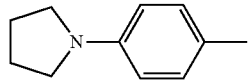 | Ph | H | H | OH | C=O | 1 | 1 |
| III-25 | 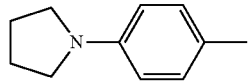 | Ph | CH₃ | H | OH | C=O | 1 | 1 |
| III-26 | 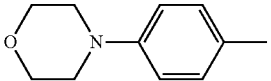 | Ph | H | H | OH | C=O | 1 | 1 |
| III-27 | 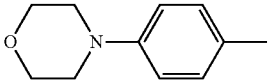 | Ph | CH₃ | H | OH | C=O | 1 | 1 |
| III-28 | 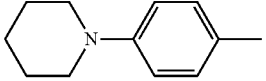 | Ph | H | H | OH | C=O | 1 | 1 |
| III-29 | 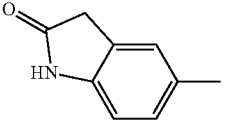 | Ph | H | H | OH | C=O | 1 | 1 |
| III-30 | 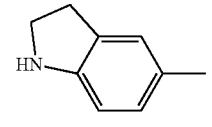 | Ph | H | H | OH | C=O | 1 | 1 |
| III-31 | Ph |  | H | H | OH | C=O | 1 | 1 |

TABLE 1-continued

| No. | Ar₁ | Ar₂ | R₁ | R₂ | A | C=B | n | m |
|---|---|---|---|---|---|---|---|---|
| III-32 | Ph | 4-OCH₃-C₆H₄- | H | H | OH | C=O | 1 | 1 |
| III-33 | Ph | 4-Cl-C₆H₄- | H | H | OH | C=O | 1 | 1 |
| III-34 | Ph | 2-pyridyl- | H | H | OH | C=O | 1 | 1 |
| III-35 | Ph | 4-(pyrrolidin-1-yl)-C₆H₄- | H | H | OH | C=O | 1 | 1 |
| III-36 | Ph | 4-(morpholin-4-yl)-C₆H₄- | H | H | OH | C=O | 1 | 1 |
| III-37 | Ph | 5-(indolin-5-yl)- | H | H | OH | C=O | 1 | 1 |
| III-38 | Ph | benzo[d][1,3]dioxol-5-yl- | H | H | OH | C=O | 1 | 1 |
| III-39 | Ph | Ph | H | CH₃ | OH | C=O | 1 | 1 |
| V-1 | 4-H₃CO-C₆H₄- | Ph | H | H | OH | CH—OH | 1 | 1 |
| V-2 | 4-AcHN-C₆H₄- | Ph | H | H | OH | CH—OH | 1 | 1 |
| V-3 | (Ph)₂CH— | Ph | H | H | OH | CH—OH | 1 | 1 |
| V-4 | benzo[d][1,3]dioxol-5-yl- | Ph | H | H | OH | CH—OH | 1 | 1 |
| V-5 | 2-OCH₃-C₆H₄- | Ph | H | H | OH | CH—OH | 0 | 1 |
| V-6 | indolin-5-yl- | Ph | H | H | OH | CH—OH | 1 | 1 |
| V-7 | 4-(pyrrolidin-1-yl)-C₆H₄- | Ph | CH₃ | H | OH | CH—OH | 1 | 1 |

TABLE 1-continued
| No. | Ar₁ | Ar₂ | R₁ | R₂ | A | C=B | n | m |
|---|---|---|---|---|---|---|---|---|
| V-8 | 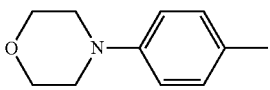 | Ph | CH₃ | H | OH | CH—OH | 1 | 1 |
| VIII-1 | 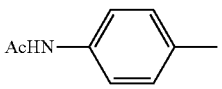 | Ph | H | H | OCH₃ | C=O | 1 | 1 |
| VIII-2 | 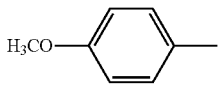 | Ph | CH₃ | H | OCH₃ | C=O | 1 | 1 |
| VIII-3 | 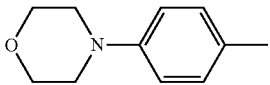 | Ph | CH₃ | H | OCH₃ | C=O | 1 | 1 |
| IX-1 | 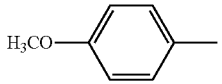 | Ph | CH₃ | H | F | C=O | 1 | 1 |
| IX-2 | 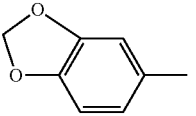 | Ph | H | H | F | C=O | 1 | 1 |
| IX-3 | 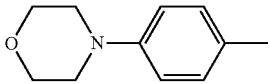 | Ph | CH₃ | H | F | C=O | 1 | 1 |
| IX-4 | 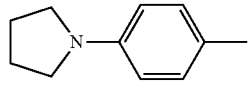 | Ph | CH₃ | H | F | C=O | 1 | 1 |
| IX-5 | 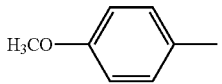 | Ph | CH₃ | H | Cl | C=O | 1 | 1 |
| IX-6 | 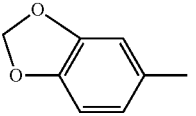 | Ph | H | H | Cl | C=O | 1 | 1 |
| IX-7 | 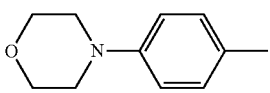 | Ph | CH₃ | H | Cl | C=O | 1 | 1 | wherein further preferable compounds include:
III-5 N-p-aminobenzyl-4-benzoylmethyl-4-piperidinol
III-7 N-diphenylmethyl-4-benzoylmethyl-4-piperidinol
III-15 N-p-methoxybenzyl-4-benzoylmethyl-4-piperidinol
V-3 N-diphenylmethyl-4-(2-hydroxy-2-phenylethyl)-4-piperidinol
IX-1 N-(1-(p-methoxyphenyl)ethyl)-4-benzoylmethyl-4-fluoropiperidine The compounds of the present invention can be synthesized through the following methods:

Scheme 1:

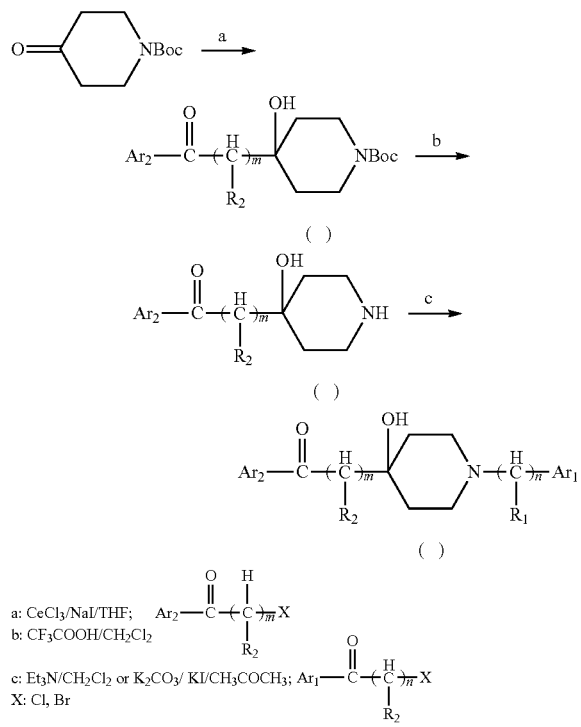

The mentioned compounds are prepared by using tert-butoxycarbonyl protected 4-piperidones as starting materials, which are subjected to a nucleophilic addition reaction firstly with the corresponding aromatic carbonyl halides, removing the protective group through an acidic hydrolysis and then subjected to a N-alkylation with the corresponding halides to obtain the target compound (III). Using a cerium chloride-sodium iodide system mediates a reaction of formation of a carbon-carbon bond between α-halo ketones and cyclic ketone, which is explained in corresponding references in details (J. CHEM. SOC. PERKIN TRANS. I, 1473, 1987). The present invention applies the method to the formation of a carbon-carbon bond between aromatic carbonyl halides and derivatives of 4-piperidone, and synthesizes a series of compounds having special and novel structures. Such a synthesizing reaction requires mild reaction conditions, needs a short reaction time, can be operated simply and has yield of 30-50%. N-alkylation normally uses chloroform as a solvent, and triethylamine as an acid scavenger, or alternatively, uses polar aprotic solvents such as acetone, dioxane, DMF, DMSO, etc. as a reaction solvent that are hardly solvated by the nucleophile agent, and K$_2$CO$_3$ as an acid scavenger. The reaction can be carried out at a temperature between 50 and 100° C. with yield of about 50-80%. Higher reaction temperature and longer reaction time will affect quality and yield of the product.

Scheme 2:

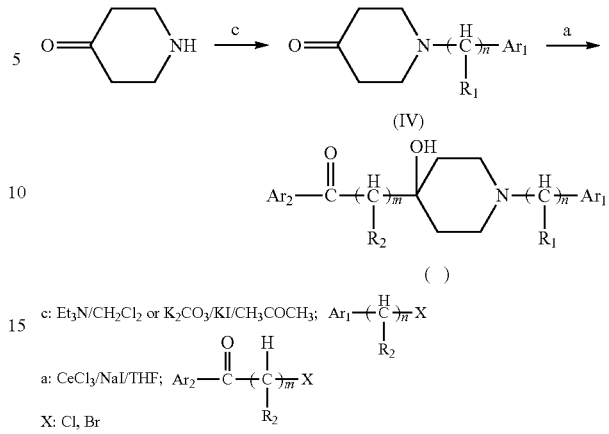

The mentioned compounds are prepared by using 4-piperidones as starting materials, which are subjected to N-alkylation firstly with the corresponding halides, and then to a nucleophilic reaction with the corresponding aromatic carbonyl halides to obtain the target compound (III). A N-alkylation reaction normally uses dichloromethane or chloroform as a solvent, and triethylamine as an acid scavenger for reaction. When the substituents have large spatial steric hindrance, polar aprotic solvents such as acetone, DMF, dioxane, etc. can be used as a reaction solvent, and K$_2$CO$_3$ as an acid scavenger. The reaction can be carried out at a temperature of between 20 and 100° C. with yield of 50-90%. Higher reaction temperature, longer reaction time, and stronger basicity of an acid scavenger will bring more side-reactions and affect quality and yield of the product.

The halogenated arylformylalkyl compounds in a can be available commercially, or can be prepared through conventional methods recorded in references, such as to conduct a halogenation reaction between bromine or cupric bromide and the corresponding aralkyl-ketones.

The halogenated arylalkyl compounds in a can be available commercially, or can be prepared through conventional methods recorded in references, such as to conduct a halogenation reaction between bromine and the corresponding arylalkyl compounds or between thionyl chloride, hydrochloric acid, phosphorus trichloride, phosphorus pentachloride, phosphorus tribromide, hydrobromic acid, etc. and the corresponding arylalkanol compounds.

Target compounds III-1 to III-39 can be obtained through steps in Scheme 1 and Scheme 2.

Scheme 3:

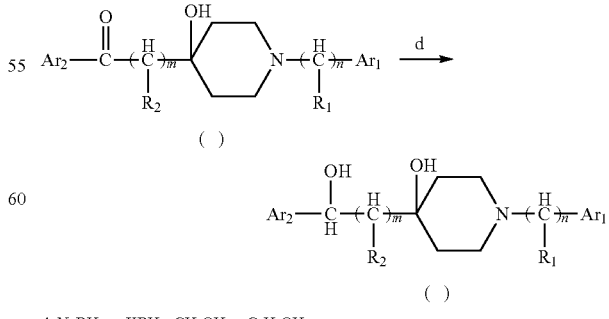

The mentioned compounds are prepared by firstly using the method in Scheme 1 to obtain the intermediate compound (III), which is then subjected to a reduction reaction using sodium borohydride or potassium borohydride to obtain the target compound (V). Target compounds V-1 to V-8 are obtained through the above steps.

Scheme 4:

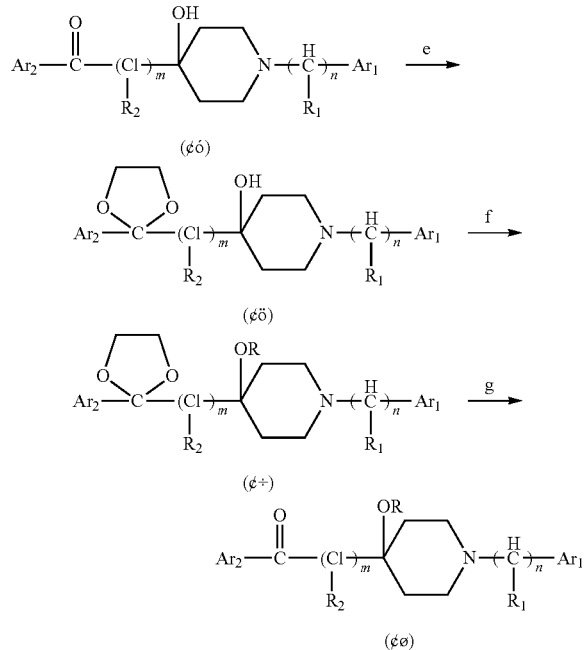

e: HOCH$_2$CH$_2$OH, p-CH$_3$C$_6$H$_4$COOH
f: RI, 60% NaH
G: HCl/C$_2$H$_5$OH

The mentioned compounds are prepared by firstly using the method in Scheme 1 to obtain the intermediate compound (III), and the keto carbonyl group therein is then protected through ethylene glycol. The protected compound is subjected to an alkylation reaction and then a deprotection reaction to prepare the target compound (VIII). Target compounds VIII-1 to VIII-3 are obtained through the above steps.

Scheme 5:

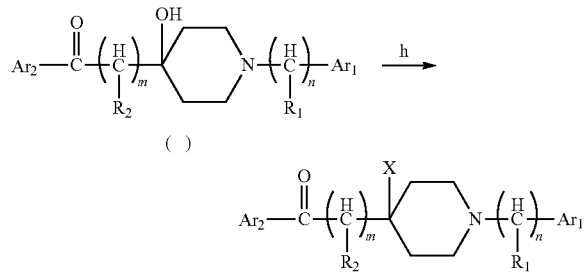

X: F, Cl, Br
h: DAST or SOCl$_2$ or PBr$_3$, CH$_2$Cl$_2$;

The mentioned compounds are prepared by firstly using the method in Scheme 1 to obtain the intermediate compound (III), which is then subjected to a halogenation reaction using halogenating reagent (fluorinating reagent DAST, chloriding agent SOCl$_2$, brominating agent PBr$_3$, etc.) to prepare the target compound (IX). Target compounds IX-1 to IX-7 can be obtained through above steps.

During preparation of the compounds (III) having the novel structure, the present invention uses N-substituted piperidones as starting materials and a reaction of formation of a C—C bond of the corresponding α-halo ketone in a cerium chloride-sodium iodide system. The present invention applies the method for the first time to the above reaction of formation of a C—C bond wherein nitrogen atom containing-piperidone compounds are used as starting materials, and to the synthesis of compounds (III) and important intermediate compounds (II) thereof. The application of the above new synthesis method synthesizes compounds III-1 to III-39.

Said reaction uses N-substituted piperidones and α-halo ketones as starting materials at a molar ratio of 0.5:1 to 2:1. It can have the highest yield when reacting at an equimolar ratio of 1:1.

Said method uses a cerium chloride-sodium iodide system, the CeCl$_3$/NaI molar ratio is in the range of 1:1 to 1:5. And it can have a good yield when the ratio is 1:3.

The solvent used in said method includes ether solvents such as THF, diethyl ether, dioxane, etc.

The reaction temperature of said method is between 0 and 100° C., and the reaction time is between 0.5 and 10 hours.

Animal tests prove that the aralkyl piperidine derivatives of the present invention can be used for the preparation of antalgic or sedative medicament.

The aralkyl piperidine derivatives of the present invention can also be used for the preparation of medicament for treating other disorders of central nervous system such as for the treatment of neuropathic pain, mania, anxiety, various depressions, schizophrenia, Parkinson's disease (PD), Huntington disease (HD), Alzheimer's disease, senile dementia, Alzheimer's dementia, memory disorders, executive dysfunction, vascular dementia and other dementia, and dysfunctional diseases associated to intelligence, study or memory.

The present invention finds that most of the new compounds based on arylalkyl piperidines series show a stronger effect of anti-pain twisting response in a pharmacological model of chemicals-caused pain of mice, and have antalgic and calm activity. And test results in a pharmacological model of hot plate in mice also show that the compounds have antalgic function.

Study results of animal models show that III-15 has a significant antalgic effect and can be absorbed well when administered orally. III-15 shows no drug resistance after multiple doses, and has low drug dependence potential, and a negative Ames test result and a higher therapeutic index, which can be developed as a novel non-addictive antalgic agent.

The derivative of the present invention can be applied to a patient in need of the treatment in form of a composition through an oral or injection route, etc. The dose generally is 0.5 to 10 mg/day/kg of body weight. The specific dose can be determined by a doctor according to the disease state, age of a patient, etc.

The said composition contains a therapeutically effective amount of the derivative of the present invention as an active ingredient, and contains one or more pharmaceutically acceptable conventional carrier(s).

The said carriers are conventional carriers commonly used in medical field, such as diluents, excipients such as water, etc; binders such as cellulose derivatives, gelatin, polyvinylpyrrolidone, etc; fillers such as starch, etc.; disintegrants such as calcium carbonate, sodium bicarbonate; and lubricants such as calcium stearate or magnesium stearate, etc. In addition, other adjuvants such as flavors and sweeteners can be added into the composition. The composition can be formulated to a conventional solid formulation such as tablets, powder or capsules when for oral administration, and can be formulated to injections when for injection.

Various dosage forms of the composition of the present invention can be prepared through conventional methods in medical field, wherein the amount of the active ingredient is between 0.1% and 99.5% (weight ratio).

The present inventor finds that the derivative of the present invention has less toxicity and a low neural side effect.

MODE OF CARRY OUT THE INVENTION

General Method One

Preparation of 4-arakylformylalkyl-4-piperidinol (II) hydrochloride

Anhydrous cerium chloride (0.99 g, 4.0 mmol) and sodium iodide (1.8 g, 12.0 mmol) are added to 10 ml of anhydrous tetrahydrofuran solvent to form a suspension. Halogenated arakylformylalkyls (4.0 mmol) and N-tert-butoxycarbonyl-4-piperidone (0.80 g, 4.0 mmol) are dissolved into 10 ml of anhydrous tetrahydrofuran, and the solution is added dropwise to the above suspension for reacting at room temperature for two hours. The reaction is terminated with 20 ml of a saturated aqueous solution of sodium thiosulfate, evaporated under reduced pressure to remove tetrahydrofuran, and extracted with chloroform (3×20 ml). The organic phase is combined, washed with water (1×10 ml) and then with saline solution (1×10 ml), dried, filtered, and evaporated to remove the solvent to obtain the product as a red-brown oil.

The above oily product is dissolved into 5 ml of dichloromethane, and cooled in an ice-water bath with temperature controlled at below 10° C. Thereto trifluoroacetic acid (40 mmol) is added dropwise, after completion of addition, the reaction is allowed to warm to room temperature and stirred for 0.5 hour. The reaction is cooled in an ice-water bath with temperature controlled at below 10° C., and thereto a saturated aqueous solution of sodium carbonate is added dropwise to adjust PH to >10. After extraction with ethyl acetate (6×20 ml), the organic phase is combined and washed with a saturated saline solution (1×20 ml). The ethyl acetate solution is dried over anhydrous sodium sulfate, filtered, concentrated to 20 ml, and adjusted to PH<3 with HCl/$C_2H_5OH$ (5N). A solid is precipitated and filtered to obtain target compounds (II) with yield of 30-42%.

General Method Two

Preparation of N-arylalkyl-4-arakylformylalkyl-4-piperidinol (III) hydrochloride 4-arakylformylalkyl-4-piperidinol (II) hydrochloride (10 mmol), halogenated arylalkyls (11 mmol), potassium iodide (1 mmol) and anhydrous $K_2CO_3$ (35 mmol) are placed in DMF (50 ml) or anhydrous acetone (80 ml), and the reaction is stirred at 25-80° C. for 8-12 hours, filtrated, evaporated under reduced pressure to remove the solvent, added thereto 50 ml of water, and extracted with AcOEt (100 ml×3). The AcOEt layers are combined, washed with 20 ml of water and 30 ml of saturated NaCl solution, dried over $MgSO_4$, filtered, and evaporated to remove the solvent. The residue is dissolved by adding 30 ml of ethyl acetate and adjusted to pH=2 with HCl/$C_2H_5OH$ (5N). The precipitated solids are filtered and recrystallized in ethanol/water or ethanol/ethyl acetate to obtain the target compound (III) with yield of 60-85%.

General Method Three

Preparation of N-arylalkyl-4-arakylformylalkyl-4-piperidinol (III) hydrochloride Anhydrous cerium chloride (0.99 g, 4.0 mmol) and sodium iodide (1.8 g, 12.0 mmol) are added to 10 ml of anhydrous tetrahydrofuran as a solvent to form a suspension. Halogenated arakylformylalkyls (4.0 mmol) and N-arylalkyl-4-piperidone (4.0 mmol) are dissolved into 10 ml of anhydrous tetrahydrofuran, and the solution is added dropwise to the above suspension for reacting at room temperature for 2 hours. The reaction is terminated with 20 ml of a saturated aqueous solution of sodium thiosulfate and evaporated under reduced pressure to remove tetrahydrofuran. After extraction with chloroform (3×20 ml), the organic phase is combined, washed with water (1×10 ml) and then with a saturated saline solution (1×10 ml), dried, filtered, and evaporated to remove solvent. The residue is dissolved by adding 20 ml of ethyl acetate and adjusted to pH=2 with HCl/$C_2H_5OH$ (5N). The precipitated solids are filtered and recrystallized in ethanol/water or ethanol/ethyl acetate to obtain N-arylalkyl-4-arakylformylalkyl-4-piperidinol hydrochloride with yield of 30-40%.

General Method Four

Preparation of N-arylalkyl-4-(2-hydroxy-2-phenyl-ethyl)-4-piperidinol (V) hydrochloride N-arylalkyl-4-benzoylmethyl-4-piperidinol (III) (4.0 mmol) is dissolved into 30 ml of an ethanol solution, and thereto sodium borohydride (4.4 mmol) is added in portion, and the reaction is mixed and thereafter stirred at room temperature until the reaction is complete. The reaction is cooled in an ice-water bath with temperature controlled at below <20° C. and thereto 3N hydrochloride is added dropwise to adjusting to PH=4, and stirred for 0.5 hour. After adjusting with a saturated aqueous solution of sodium bicarbonate to be neutral, the reaction is added 10 ml of water, rotarily evaporated to remove ethanol, adjusted with 10% of an aqueous solution of NaOH to PH=10. After extraction with ethyl acetate (2×20 ml), the organic phase is combined, washed with 20 ml of a saturated brine solution, dried over anhydrous magnesium sulfate, filtered, evaporated to remove ethyl acetate till having about 20 ml of a residue. The residue is adjusted with HCl/$C_2H_5OH$ (5N) to pH=2. The precipitated solids are filtered and recrystallized in ethanol/water or ethanol/ethyl acetate to obtain N-arylalkyl-4-(2-hydroxy-2-phenylethyl)-4-piperidinol (V) hydrochloride with yield of 60-80%.

General Method Five

Preparation of N-arylalkyl-4-benzoylmethyl-4-methoxylpiperidine (VIII) hydrochloride N-arylalkyl-4-benzoylmethyl-4-piperidinol (III) (4.0 mmol) and ethylene glycol (8.0 mmol) are dissolved into 30 ml of benzene, thereto p-toluene sulfonic acid (0.20 mmol) is added, and the reaction is heated to reflux until benzene entrainment distillation of water is complete. The reaction solution is cooled to room temperature, washed with a saturated aqueous solution of sodium bicarbonate (2×20 ml), water (1×20 ml) and a saturated brine solution (1×20 ml), and evaporated to dryness. The residue is dissolved into 20 ml of benzene, added thereto 60% of NaH (4.0 mmol) slowly and stirred for 0.5 hour. The reaction solution is added dropwise a benzene solution of iodomethane (5.0 mmol, 5 ml) and stirred at room temperature until the reaction is complete. The reaction is washed with water (1×20 ml) and then with a saturated brine solution (1×20 ml), and evaporated to dryness.

The residue is dissolved into and treated with 10 ml of hydrochloric acid (1 mol/L) to deprotect the ethylene glycol protecting group, alkalized, extracted with ethyl acetate, further adjusted with HCl/$C_2H_5$OH (5N) to pH=2. A solid is obtained after evaporating out the solvent, and recrystallized in ethanol/water or ethanol/ethyl acetate to obtain N-arylalkyl-4-benzoylmethyl-4-methoxylpiperidine (VIII) hydrochloride with total yield of 40-50%.

General Method Six

Preparation of
N-arylalkyl-4-benzoylmethyl-4-fluoropiperidine (IX)
hydrochloride N-arylalkyl-4-benzoylmethyl-4-piperidinol (III) (4.0 mmol) is dissolved into 20 ml of anhydrous dichloromethane, cooled with dry ice-acetone with temperature controlled at below <−70° C. The reaction solution is added dropwise a dichloromethane solution (8 mol, 25 ml) of DAST under protection of nitrogen gas. After completion of addition, the temperature is maintained at −75° C. and reacting one hour. The temperature is raised slowly and maintained at −10° C. and reacting two hours. The reaction is added dropwise 30 ml of water and 10 ml of a saturated aqueous solution of potassium carbonate. After extraction with $Et_2O$ (4×30 ml), the organic phase is combined, washed with a saturated brine solution (1×30 ml), dried, concentrated, and separated with column chromatography eluting with petroleum ether/ethyl acetate to obtain product as an oil. A salt is formed after acidifying a residue with HCl/$C_2H_5$OH, and recrystallized in ethanol/ethyl acetate to obtain N-arylalkyl-4-benzoylmethyl-4-fluoropiperidine (IX) hydrochloride with yield of 35-50%.

General Method Seven

Preparation of
N-arylalkyl-4-benzoylmethyl-4-chloropiperidine
(IX) hydrochloride N-arylalkyl-4-benzoylmethyl-4-piperidinol (III) (4.0 mmol) is dissolved into 20 ml of anhydrous dichloromethane and cooled in an ice-water bath with temperature controlled at 0° C. The reaction solution is added dropwise dichloromethane solution (8 mol, 25 ml) of $SOCl_2$. After completion of addition, the reaction is allowed to warm to room temperature slowly and reacting one hour. The reaction is added dropwise 30 ml of water and 10 ml of a saturated aqueous solution of potassium carbonate, and stirred for 30 minutes. A liquid separation occurs on standing and the water phase is extracted with $CH_2Cl_2$ (4×30 ml). The organic phase is combined, washed with a saturated brine solution (1×30 ml), dried, and concentrated to dryness. A salt is formed after acidifying a residue with HCl/$C_2H_5$OH, and recrystallized in ethanol/ethyl acetate to obtain N-arylalkyl-4-benzoylmethyl-4-chloropiperidine (IX) hydrochloride with yield of 30-45%.

Example 1

III-1 preparation of N-benzyl-4-benzoylmethyl-4-piperidinol hydrochloride and N-benzyl-4-benzoylmethyl-4-piperidinol hydrobromide Anhydrous cerium chloride (1.98 g, 8.0 mmol) and sodium iodide (3.6 g, 24.0 mmol) are added to 20 ml of anhydrous tetrahydrofuran as a solvent to form a suspension. 1.60 g of bromoacetophenone (8.0 mmol) and 1.51 g (8.0 mmol) of N-benzyl-4-piperidone are dissolved into 10 ml of anhydrous tetrahydrofuran, and the solution is added dropwise to the above suspension. Operating according to the methods of synthesis and post-treatment in General Method three obtains 1.05 g of a white crystal, with yield of 36%.

N-benzyl-4-benzoylmethyl-4-piperidinol is prepared through the above method and forms a salt by acidifying with hydrobromic acid/ethanol solution in post-treatment procedure, and recrystallized in ethyl acetate/ethanol to obtain a white crystal, with yield of 32%.

Element analysis: $C_{20}H_{23}NO_2.HCl.H_2O$ (calculated value %: C, 66.01; H, 7.20; N, 3.85; Cl, 9.74; found value %: C, 65.83; H, 7.07; N, 3.96; Cl, 9.82) $C_{20}H_{23}NO_2.HBr.H_2O$ (calculated value %: C, 58.83; H, 6.42; N, 3.43; Br, 19.57. Found value %: C, 58.63; H, 6.57; N, 3.65; Br, 19.82)

$^1$HNMR (DMSO-$d_6$): δ1.80-2.10 (m, 4H, piperidine-H), 3.00-3.20 (m, 4H, piperidine-H), 3.13 (s, 2H, $CH_2CO$), 4.25 (s, 2H, $PhCH_2$), 5.01 (s, 1H, piperidine-N.HCl), 7.20-8.10 (m, 10H, ArH), 9.5-12.0 (2B, 1H, piperidine-OH).

MS: m/z 310 (M+1)

Example 2

III-2
N-p-chlorobenzyl-4-benzoylmethyl-4-piperidinol
hydrochloride 4-benzoylmethyl-4-piperidinol (II) is firstly prepared according to the method of synthesis and post-treatment in General Method one. Thereafter, 1.76 g (8.8 mmol) of p-chlorobenzyl bromide and 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 8 hours. Operating according to the post-treatment procedure in General Method two obtains 2.25 g of a white crystal, with yield of 70.5%.

Element analysis: $C_{20}H_{22}ClNO_2.HCl.H_2O$ (calculated value %: C, 60.31; H, 6.33; N, 3.52; Cl, 17.80; found value %: C, 60.42; H, 6.15; N, 3.30; Cl, 17.96)

$^1$HNMR (DMSO-$d_6$): δ1.80-2.10 (m, 4H, piperidine-H), 3.00-3.20 (m, 4H, piperidine-H), 3.15 (s, 2H, $CH_2CO$), 4.25-4.40 (m, 2H, $PhCH_2$), 4.98 (s, 1H, piperidine-N.HCl), 7.20-8.10 (m, 9H, ArH), 10.5-11.5 (2B, 1H, piperidine-OH).

MS: m/z 344 (M$^+$)

Example 3

III-3
N-p-fluorobenzyl-4-benzoylmethyl-4-piperidinol
hydrochloride 4-benzoylmethyl-4-piperidinol (II) is firstly prepared according to the method of synthesis and post-treatment in General Method one. Thereafter, 1.66 (8.8 mmol) of p-fluorobenzyl bromide and 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 8 hours. Operating according to the post-treatment procedure in General Method two obtains 2.06 g of a white crystal, with yield of 67.5%.

Element analysis: $C_{20}H_{22}FNO_2.HCl.H_2O$ (calculated value %: C, 62.90; H, 6.60; N, 3.67; Cl, 9.28; found value %: C, 60.87; H, 6.45; N, 3.39; Cl, 9.56)

$^1$HNMR (DMSO-$d_6$): δ1.80-2.10 (m, 4H, piperidine-H), 3.00-3.20 (m, 4H, piperidine-H), 3.13 (s, 2H, $CH_2CO$), 4.25-4.40 (m, 2H, $PhCH_2$), 5.02 (s, 1H, piperidine-N HCl), 7.20-8.10 (m, 9H, ArH), 10.6-11.2 (2B, 1H, piperidine-OH).

MS: m/z 328 ($M^+$)

Example 4

III-4 N-p-nitrobenzyl-4-benzoylmethyl-4-piperidinol hydrochloride 4-benzoylmethyl-4-piperidinol (II) is firstly prepared according to the method of synthesis and post-treatment in General Method one. Thereafter, 1.90 (8.8 mmol) of p-nitrobenzyl bromide and 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 8 hours. Operating according to the post-treatment procedure in General Method two obtains 2.68 g of a white crystal, with yield of 81.9%.

Element analysis: $C_{20}H_{22}N_2O_4.HCl.H_2O$ (calculated value %: C, 58.75; H, 6.16; N, 6.85; Cl, 8.67; found value %: C, 58.52; H, 6.28; N, 7.04; Cl, 8.95)

$^1$HNMR (DMSO-$d_6$): δ1.80-2.10 (m, 4H, piperidine-H), 3.00-3.20 (m, 4H, piperidine-H), 3.13 (s, 2H, $CH_2CO$), 4.25 (s, 2H, $PhCH_2$), 7.20-8.10 (m, 9H, ArH), 10.5-11.5 (2B, 1H, piperidine-OH).

MS: 355 (M+1)

Example 5

III-5
N-p-aminobenzyl-4-benzoylmethyl-4-piperidinol hydrochloride

N-p-nitrobenzyl-4-benzoylmethyl-4-piperidinol (III-4) hydrochloride is firstly prepared according to the method of synthesis and post-treatment in Example 4. Thereafter, 1.23 g of (3.0 mmol) (III-4) hydrochloride and 3.05 g (13.5 mmol) of stannous chloride dihydrate are placed in 80 ml of an aqueous solution of methanol (50%), and reacting at 40-50° C. for 20 hours. The reaction solution is adjusted with an aqueous solution of NaOH (5N) to be neutral, evaporated to remove methanol, and further adjusted with an aqueous solution of NaOH (5N) to pH=12. After extraction with ethyl acetate (4×20 ml), the organic phase is combined, washed with a saturated brine solution (1×20 ml), dried over anhydrous $MgSO_4$, filtered, and evaporated to remove the solvent to leave about 30 ml. The residue is adjusted with $HCl/C_2H_5OH$ (5N) to pH=2, and filtered to obtain a crude, which is recrystallized in ethanol/water to obtain 0.75 g of a white crystal, with yield of 57.7%.

Element analysis: $C_{20}H_{22}N_2O_2.2HCl.H_2O$ (calculated value %: C, 55.43; H, 6.98; N, 6.46; Cl, 16.36; found value %: C, 55.56; H, 6.72; N, 6.18; Cl, 16.69)

$^1$HNMR (DMSO-$d_6$): δ1.80-2.10 (m, 4H, piperidine-H), 3.00-3.20 (m, 4H, piperidine-H), 3.16 (s, 2H, $CH_2CO$), 4.03-4.10 (m, 2H, $PhCH_2$), 4.96 (s, H, piperidine-N.HCl), 5.29 (s, 2H, $Ar_1$—$NH_2$), 7.20-8.10 (m, 9H, ArH), 9.6-10.2 (2B, 1H, piperidine-OH).

MS: 325 (M+1).

Example 6

III-6 N-p-acetylaminobenzyl-4-benzoylmethyl-4-piperidinol hydrochloride

N-p-aminobenzyl-4-benzoylmethyl-4-piperidinol(III-5) hydrochloride is prepared according to the method of synthesis and post-treatment in Example 5, and 1.34 g (3.0 mmol) of (III-5) hydrochloride in dissolved into 10 ml of water, thereto potassium carbonate is added to adjust to PH>12. After extraction with ethyl acetate (4×20 ml), the organic phase is combined, washed with a saturated brine solution (1×20 ml), dried over anhydrous $MgSO_4$, filtered, evaporated to leave about 30 ml. The residue is added dropwise 0.31 g (3.0 mmol) of acetic anhydride. The reaction is stirred at room temperature for 1 hour and evaporated to obtain a solid crude, which is recrystallized in ethanol/water to obtain 1.12 g of a white crystal, with yield of 88.7%.

Element analysis: $C_{22}H_{26}N_2O_3.HCl.H_2O$ (calculated value %: C, 62.77; H, 6.94; N, 6.66; Cl, 8.42; found value %: C, 62.56; H, 7.08; N, 6.92; Cl, 8.84)

$^1$HNMR (DMSO-$d_6$): δ1.80-2.10 (m, 4H, piperidine-H), 2.04 (s, 3H), 3.00-3.20 (m, 4H, piperidine-H), 3.16 (s, 2H, $CH_2CO$), 4.03-4.10 (m, 2H, $PhCH_2$), 4.95 (s, H, piperidine-N.HCl), 8.09 (s, 1H, $Ar_1$—NH), 7.20-8.10 (m, 9H, ArH), 9.6-10.2 (2B, 1H, piperidine-OH).

MS: 267 (M+1)

Example 7

III-7
N-diphenylmethyl-4-benzoylmethyl-4-piperidinol hydrochloride 4-benzoylmethyl-4-piperidinol (II) is firstly prepared according to the method of synthesis and post-treatment in General Method one. Thereafter, 1.98 g (8.8 mmol) of diphenylmethyl bromide and 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.53 g of a white crystal, with yield of 74.9%.

Element analysis: $C_{26}H_{27}NO_2.HCl$ (calculated value %: C, 74.01; H, 6.69; N, 3.32; Cl, 8.40; found value %: C, 74.12; H, 6.89; N, 3.51; Cl, 8.80)

$^1$HNMR (DMSO-$d_6$): δ1.80-2.10 (m, 4H, piperidine-H), 3.00-3.20 (m, 4H, piperidine-H), 3.16 (s, 2H, $CH_2CO$), 4.03-4.10 (m, H, $Ph_2CH$), 4.95 (s, H, piperidine-N.HCl), 5.29 (s, 2H, $Ar_1$—$NH_2$), 7.20-8.10 (m, 15H, ArH), 9.6-10.2 (2B, 1H, piperidine-OH).

MS: m/z 286 (M+1).

Example 8

III-8
N-(2-pyridyl)methyl-4-benzoylmethyl-4-piperidinol hydrochloride 4-benzoylmethyl-4-piperidinol (II) is firstly prepared according to the method of synthesis and post-treatment in General Method one. Thereafter, 1.51 g (8.8 mmol) of 2-bromomethylpyridine and 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.16 g of a white crystal, with yield of 67.3%.

Element analysis: $C_{19}H_{22}N_2O_2 \cdot 2HCl \cdot H_2O$ (calculated value %: C, 56.86; H, 6.53; N, 6.98; Cl, 17.67; found value %: C, 56.68; H, 6.77; N, 6.83; Cl, 17.84)

$^1$HNMR (DMSO-$d_6$): δ1.80-2.10 (m, 4H, piperidine-H), 3.00-3.20 (m, 4H, piperidine-H), 3.16 (s, 2H, $CH_2CO$), 4.06-4.13 (m, 2H), 4.97 (s, H, piperidine-N.HCl), 7.20-8.60 (m, 9H), 9.6-10.2 (2B, 1H, piperidine-OH).

MS: m/z 311 (M+1)

Example 9

III-9
N-(2-pyrimidinyl)-4-benzoylmethyl-4-piperidinol hydrochloride 4-benzoylmethyl-4-piperidinol (II) is firstly prepared according to the method of synthesis and post-treatment in General Method one. Thereafter, 1.40 g (8.8 mmol) of 2-bromopyrimidine and 1.75 g (8.0 mmol) of 4-benzoylmethyl-4-piperidinol, 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 1.67 g of a white crystal, with yield of 59.4%.

Element analysis: $C_{18}H_{21}N_3O_2 \cdot HCl \cdot H_2O$ (calculated value %: C, 58.03; H, 6.30; N, 11.94; Cl, 10.08; found value %: C, 58.27; H, 6.49; N, 11.78; Cl, 10.22)

$^1$HNMR (DMSO-$d_6$): δ1.80-2.10 (m, 4H, piperidine-H), 3.00-3.20 (m, 4H, piperidine-H), 3.16 (s, 2H, $CH_2CO$), 4.97 (s, H, piperidine-N.HCl), 7.20-8.70 (m, 8H), 9.6-10.2 (2B, 1H, piperidine-OH).

MS: m/z 312 (M+1)

Example 10

III-10 N-(2-pyrimidinyl)methyl-4-benzoylmethyl-4-piperidinol hydrochloride 4-benzoylmethyl-4-piperidinol (II) is firstly prepared according to the method of synthesis and post-treatment in General Method one. Thereafter, 1.52 g (8.8 mmol) of 2-bromomethylpyrimidine and 1.75 g (8.0 mmol) of 4-benzoylmethyl-4-piperidinol, 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.25 g of a white crystal, with yield of 76.8%.

Element analysis: $C_{18}H_{21}N_3O_2 \cdot HCl \cdot H_2O$ (calculated value %: C, 59.09; H, 6.61; N, 11.49; Cl, 9.69; found value %: C, 59.27; H, 6.89; N, 11.68; Cl, 10.02)

$^1$HNMR (DMSO-$d_6$): δ1.80-2.10 (m, 4H, piperidine-H), 3.00-3.20 (m, 4H, piperidine-H), 3.16 (s, 2H, $CH_2CO$), 4.03-4.10 (m, 2H, $PhCH_2$), 4.97 (s, H, piperidine-N.HCl), 7.20-8.70 (m, 8H), 9.6-10.2 (2B, 1H, piperidine-OH).

MS: m/z 324 (M+1)

Example 11

III-11 N-(2-quinolyl)-4-benzoylmethyl-4-piperidinol hydrochloride 4-benzoylmethyl-4-piperidinol (II) is firstly prepared according to the method of synthesis and post-treatment in General Method one. Thereafter, 1.83 g (8.8 mmol) of 2-bromoquinoline and 1.75 g (8.0 mmol) of 4-benzoylmethyl-4-piperidinol, 3.53 g (25.6 mmol) of anhydrous $K_2CO_3$ is placed in DMF (60 ml), and reacting at 120° C. for 12 hours. Operating according to the post-treatment procedure in General Method two obtains 1.58 g of a white crystal, with yield of 45.1%.

Element analysis: $C_{22}H_{22}N_2O_2 \cdot 2HCl \cdot H_2O$ (calculated value %: C, 60.42; H, 5.99; N, 6.41; Cl, 16.21; found value %: C, 60.65; H, 6.12; N, 6.24; Cl, 16.01)

$^1$HNMR (DMSO-$d_6$): δ1.80-2.10 (m, 4H, piperidine-H), 3.00-3.20 (m, 4H, piperidine-H), 3.16 (s, 2H, $CH_2CO$), 5.01 (s, H, piperidine-N.HCl), 7.20-8.50 (m, 11H), 9.6-10.2 (2B, 1H, piperidine-OH).

MS: m/z 347 (M+1).

Example 12

III-12 N-(2'-methoxyphenyl)-4-benzoylmethyl-4-piperidinol hydrochloride

Anhydrous cerium chloride (0.99 g, 4.0 mmol) and sodium iodide (1.8 g, 12.0 mmol) are added to 10 ml of anhydrous tetrahydrofuran as a solvent to form a suspension. 0.80 g (4.0 mmol) of bromoacetophenone and 0.82 g (4.0 mmol) of N-(2'-methoxyphenyl)-4-piperidone are dissolved into 10 ml of anhydrous tetrahydrofuran, and the solution is added dropwise to the above suspension. Operating according to the post-treatment procedure in General Method three obtains 0.5 g of a white crystal, with yield of 38.5%.

Element analysis: $C_{20}H_{23}NO_3 \cdot HCl$ (calculated value %: C, 66.38; H, 6.69; N, 3.87; Cl, 9.80; found value %: C, 66.16; H, 6.81; N, 4.18; Cl, 10.02)

$^1$HNMR (DMSO-$d_6$): δ1.80-2.10 (m, 4H, piperidine-H), 3.00-3.20 (m, 4H, piperidine-H), 3.15 (s, 2H, $CH_2CO$), 3.75 (s, 3H, —$OCH_3$), 4.98 (s, 1H, piperidine-N.HCl), 6.60-8.20 (m, 9H, ArH), 9.5-12.0 (2B, 1H, piperidine-OH).

MS: m/z 326 (M+1)

Example 13

III-13 N-(benzo[d][1,3]dioxol-5-ylmethyl)-4-benzoylmethyl-4-piperidinol hydrochloride 4-benzoylmethyl-4-piperidinol (II) is firstly prepared according to the method of synthesis and post-treatment in General Method one. Thereafter, 1.89 g (8.8 mmol) of 3,4-methylenedioxybenzyl bromide and 1.75 g (8.0 mmol) of 4-benzoylmethyl-4-piperidinol (II), and 3.53 g (25.6 mmol) of anhydrous $K_2CO_3$ is placed in anhydrous acetone (60 ml), and reacting at reflux for 8 hours. Operating according to the post-treatment procedure in General Method two obtains 2.13 g of a white crystal, with yield of 65.3%.

Element analysis: $C_{21}H_{23}NO_4 \cdot HCl \cdot H_2O$ (calculated value %: C, 61.84; H, 6.42; N, 3.43; Cl, 8.69; found value %: C, 61.62; H, 6.27; N, 3.73; Cl, 8.86)

$^1$HNMR (DMSO-$d_6$): δ1.80-2.10 (m, 4H, piperidine-H), 3.00-3.20 (m, 4H, piperidine-H), 3.13 (s, 2H, $CH_2CO$), 4.25

(s, 2H), 5.03 (s, 1H, piperidine-N.HCl), 5.92 (s, 2H), 6.90-8.10 (m, 8H, ArH), 9.5-11.6 (2B, 1H, piperidine-OH).

MS: m/z 354 (M+1).

Example 14

III-14 N-(3,4,5-trimethoxybenzyl)-4-benzoylmethyl-4-piperidinol hydrochloride 4-benzoylmethyl-4-piperidinol (II) is firstly prepared according to the method of synthesis and post-treatment in General Method one. Thereafter, 2.30 g (8.8 mmol) of 3,4,5-trimethoxybenzyl bromide and 1.75 g (8.0 mmol) of 4-benzoylmethyl-4-piperidinol (II), and 3.53 g (25.6 mmol) of anhydrous $K_2CO_3$ is placed in anhydrous acetone (60 ml), and reacting at reflux for 8 hours. Operating according to the post-treatment procedure in General Method two obtains 2.05 g of a white crystal, with yield of 56.5%.

Element analysis: $C_{23}H_{29}NO_5 \cdot HCl \cdot H_2O$ (calculated value %: C, 60.85; H, 7.11; N, 3.09; Cl, 7.81; found value %: C, 61.03; H, 7.40; N, 3.21; Cl, 8.04)

$^1$HNMR (DMSO-$d_6$): δ1.80-2.10 (m, 4H, piperidine-H), 3.00-3.20 (m, 4H, piperidine-H), 3.13 (s, 2H, $CH_2CO$), 3.75 (s, 9H, —$OCH_3$), 4.87 (s, 2H), 5.01 (s, 1H, piperidine-N.HCl), 6.10-8.05 (m, 7H, ArH), 9.5-12.0 (2B, 1H, piperidine-OH).

MS: m/z 400 (M+1)

Example 15

III-15 N-p-methoxybenzyl-4-benzoylmethyl-4-piperidinol hydrochloride 4-benzoylmethyl-4-piperidinol (II) is firstly prepared according to the method of synthesis and post-treatment in General Method one. Thereafter, 1.77 g (8.8 mmol) of p-methoxybenzyl bromide and 1.75 g (8.0 mmol) of 4-benzoylmethyl-4-piperidinol (II), and 3.53 g (25.6 mmol) of anhydrous $K_2CO_3$ is placed in anhydrous acetone (60 ml), and reacting at reflux for 8 hours. Operating according to the post-treatment procedure in General Method two obtains 1.93 g of a white crystal, with yield of 61.3%.

Element analysis: $C_{21}H_{25}NO_3 \cdot HCl \cdot H_2O$ (calculated value %: C, 64.03; H, 7.16; N, 3.56; Cl, 9.00; found value %: C, 64.32; H, 7.33; N, 3.80; Cl, 9.27)

$^1$HNMR (DMSO-$d_6$): δ1.80-2.10 (m, 4H, piperidine-H), 3.00-3.20 (m, 4H, piperidine-H), 3.13 (s, 2H, $CH_2CO$), 3.81 (s, 3H, —$OCH_3$), 4.25 (s, 2H), 5.01 (s, 1H, piperidine-N.HCl), 7.20-8.10 (m, 9H, ArH), 9.5-12.0 (2B, 1H, piperidine-OH).

MS: m/z 340 (M+1).

Example 16

III-16 N-(1-phenylethyl)-4-benzoylmethyl-4-piperidinol hydrochloride 4-benzoylmethyl-4-piperidinol (II) is firstly prepared according to the method of synthesis and post-treatment in General Method one. Thereafter, 1.63 g (8.8 mmol) of 1-phenethyl bromide, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.18 g of a white crystal, with yield of 72.1%.

Element analysis: $C_{21}H_{25}NO_2 \cdot HCl \cdot H_2O$ (calculated value %: C, 66.74; H, 7.47; N, 3.71; Cl, 9.38; found value %: C, 66.98; H, 7.67; N, 3.83; Cl, 9.52)

$^1$HNMR (DMSO-$d_6$): δ 1.35 (d, 3H, $CH_3$), 1.80-2.10 (m, 4H, piperidine-H), 3.00-3.20 (m, 4H, piperidine-H), 3.16 (s, 2H, $CH_2CO$), 4.03-4.10 (m, 1H, PhCH), 4.95 (s, 1H, piperidine-N.HCl), 7.20-8.10 (m, 10H, ArH), 9.6-10.2 (2B, 1H, piperidine-OH).

MS: m/z 324 (M+1)

Example 17

III-17 (R)—N-(1-phenylethyl)-4-benzoylmethyl-4-piperidinol hydrochloride 4-benzoylmethyl-4-piperidinol (II) is firstly prepared according to the method of synthesis and post-treatment in General Method one. Thereafter, 1.63 g (8.8 mmol) of R-1-phenethyl bromide, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.21 g of a white crystal, with yield of 73.1%.

Element analysis: $C_{21}H_{25}NO_2 \cdot HCl \cdot H_2O$ (calculated value %: C, 66.74; H, 7.47; N, 3.71; Cl, 9.38; found value %: C, 66.98; H, 7.67; N, 3.83; Cl, 9.52)

MS: m/z 324 (M+1)

Example 18

III-18 (S)—N-(1-phenylethyl)-4-benzoylmethyl-4-piperidinol hydrochloride 4-benzoylmethyl-4-piperidinol (II) is firstly prepared according to the method of synthesis and post-treatment General Method one. Thereafter, 1.63 g (8.8 mmol) of S-1-phenethyl bromide, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.08 g of a white crystal, with yield of 68.8%.

Element analysis: $C_{21}H_{25}NO_2 \cdot HCl \cdot H_2O$ (calculated value %: C, 66.74; H, 7.47; N, 3.71; Cl, 9.38; found value %: C, 66.98; H, 7.67; N, 3.83; Cl, 9.52)

MS: m/z 324 (M+1)

Example 19

III-19 N-(1-(4-methoxyphenyl)ethyl)-4-benzoylmethyl-4-piperidinol hydrochloride 4-benzoylmethyl-4-piperidinol (II) is firstly prepared according to the method of synthesis and post-treatment in General Method one. Thereafter, 1.89 g (8.8 mmol) of 1-(bromoethyl)-4-methoxybenzene, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.33 g of a white crystal, with yield of 71.5%.

Element analysis: $C_{22}H_{27}NO_3\cdot HCl\cdot H_2O$ (calculated value %: C, 64.77; H, 7.41; N, 3.43; Cl, 8.69; found value %: C, 64.99; H, 7.52; N, 3.31; Cl, 8.92)

$^1$HNMR (DMSO-$d_6$): δ 1.35 (d, 3H, $CH_3$), 1.80-2.10 (m, 4H, piperidine-H), 3.00-3.20 (m, 4H, piperidine-H), 3.17 (s, 2H, $CH_2CO$), 3.82 (s, 3H), 4.03-4.10 (m, 1H), 4.99 (s, 1H, piperidine-N.HCl), 7.00-8.10 (m, 9H, ArH), 9.6-11.2 (2B, 1H, piperidine-OH).

MS: m/z 354 (M+1)

Example 20

III-20 N-(1-(4-fluorophenyl)ethyl)-4-benzoylmethyl-4-piperidinol hydrochloride 4-benzoylmethyl-4-piperidinol (II) is firstly prepared according to the method of synthesis and post-treatment in General Method one. Thereafter, 1.79 g (8.8 mmol) of 1-(1-bromoethyl)-4-fluorobenzene, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.39 g of a white crystal, with yield of 75.5%.

Element analysis: $C_{21}H_{24}FNO_2\cdot HCl\cdot H_2O$ (calculated value %: C, 63.71; H, 6.87; N, 3.54; Cl, 8.96; found value %: C, 63.96; H, 6.65; N, 3.32; Cl, 9.12)

$^1$HNMR (DMSO-$d_6$): δ 1.35 (d, 3H, $CH_3$), 1.80-2.10 (m, 4H, piperidine-H), 3.00-3.20 (m, 4H, piperidine-H), 3.16 (s, 2H, $CH_2CO$), 4.03-4.10 (m, 1H, PhCH), 5.01 (s, 1H, piperidine-N.HCl), 7.20-8.10 (m, 9H, ArH), 9.6-10.2 (2B, 1H, piperidine-OH).

MS: m/z 342 (M+1)

Example 21

III-21 N-(1-(4-aminophenyl)ethyl)-4-benzoylmethyl-4-piperidinol hydrochloride 4-benzoylmethyl-4-piperidinol (II) is firstly prepared according to the method of synthesis and post-treatment in General Method one. Thereafter, 2.02 g (8.8 mmol) of 1-bromoethyl-4-nitrobenzene, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.64 g of white crystal with yield of 78.1%.

2.64 g (6.2 mmol) of N-(p-nitrophenylethyl)-4-benzoylmethyl-4-piperidinol hydrochloride and 5.62 g (25.0 mmol) of stannous chloride dihydrate is placed in 80 ml of an aqueous solution of methanol (50%), and reacting at 40-50° C. for 20 hours. The reaction solution is adjusted with an aqueous solution of NaOH (5N) to be neutral, evaporated to remove methanol, and further adjusted with an aqueous solution of NaOH (5N) to PH=12. After extraction with ethyl acetate (4×20 ml), the organic phase is combined, washed with a saturated brine solution (1×20 ml), dried over anhydrous $MgSO_4$, filtered, and evaporated to leave about 30 ml. The residue is adjusted with $HCl/C_2H_5OH$ (5N) to pH=2 and filtered to obtain a crude, which recrystallized in ethanol/water to obtain 1.34 g of a white crystal, with yield of 50.3%.

Element analysis: $C_{21}H_{26}N_2O_2\cdot 2HCl\cdot H_2O$ (calculated value %: C, 58.74; H, 7.04; N, 6.52; Cl, 16.51; found value %: C, 58.91; H, 6.86; N, 6.50; Cl, 16.83)

$^1$HNMR (DMSO-$d_6$): δ 1.35 (d, 3H, $CH_3$), 1.80-2.10 (m, 4H, piperidine-H), 3.00-3.20 (m, 4H, piperidine-H), 3.17 (s, 2H, $CH_2CO$), 4.03-4.10 (m, 1H, PhCH), 4.99 (s, 1H, piperidine-N.HCl), 5.30 (s, 2H, $Ar_1$-$NH_2$), 7.20-8.10 (m, 9H, ArH), 9.6-11.2 (2B, 1H, piperidine-OH).

MS: m/z 339 (M+1)

Example 22

III-22 N-(1-(benzo[d][1,3]dioxol-5-yl)ethyl)-4-benzoylmethyl-4-piperidinol hydrochloride 4-benzoylmethyl-4-piperidinol (II) is firstly prepared according to the method of synthesis and post-treatment in General Method one. Thereafter, 2.02 g (8.8 mmol) of 1-bromoethyl-3,4-methylenedioxybenzene, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.23 g of a white crystal, with yield of 66.2%.

Element analysis: $C_{21}H_{26}N_2O_2\cdot 2HCl\cdot H_2O$ (calculated value %: C, 62.63; H, 6.69; N, 3.32; Cl, 8.40; found value %: C, 62.74; H, 6.85; N, 3.52; Cl, 8.69)

$^1$HNMR (DMSO-$d_6$): δ 1.36 (d, 3H, $CH_3$), 1.80-2.10 (m, 4H, piperidine-H), 3.00-3.20 (m, 4H, piperidine-H), 3.17 (s, 2H, $CH_2CO$), 4.03-4.10 (m, 1H, PhCH), 4.97 (s, 1H, piperidine-N.HCl), 5.92 (s, 2H), 6.80-8.10 (m, 8H, ArH), 9.6-11.2 (2B, 1H, piperidine-OH).

MS: m/z 368 (M+1)

Example 23

III-23 N-(2-naphthylmethyl)-4-benzoylmethyl-4-piperidinol hydrochloride 4-benzoylmethyl-4-piperidinol (II) is firstly prepared according to the method of synthesis and post-treatment in General Method one. Thereafter, 2.07 g (8.8 mmol) of 2-(bromomethyl)-naphthalene, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.15 g of a white crystal, with yield of 64.0%.

Element analysis: $C_{25}H_{27}NO_2\cdot HCl\cdot \frac{1}{2}H_2O$ (calculated value %: C, 71.67; H, 6.98; N, 3.34; Cl, 8.46; found value %: C, 71.28; H, 7.06; N, 3.12; Cl, 8.59)

$^1$HNMR (DMSO-$d_6$): δ1.80-2.10 (m, 4H, piperidine-H), 3.00-3.20 (m, 4H, piperidine-H), 3.14 (s, 2H, $CH_2CO$), 4.24 (s, 2H, $PhCH_2$), 5.01 (s, 1H, piperidine-N.HCl), 7.10-8.20 (m, 12H, ArH), 9.9-11.5 (2B, 1H, piperidine-OH).

MS: m/z 374 (M+1)

Example 24

III-24 N-(4-(1-pyrrolidinyl)benzyl)-4-benzoylmethyl-4-piperidinol hydrochloride 4-benzoylmethyl-4-piperidinol (II) is firstly prepared according to the method of synthesis and post-treatment in General Method one. Thereafter, 2.11 g (8.8 mmol) of 4-(1-pyrrolidinyl)benzyl bromide, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.67 g of a white crystal, with yield of 71.0%.

Element analysis: $C_{24}H_{30}N_2O_2 \cdot 2HCl \cdot H_2O$ (calculated value %: C, 61.40; H, 7.30; N, 5.97; Cl, 15.10; found value %: C, 61.28; H, 7.45; N, 6.07; Cl, 15.34)

$^1$HNMR (DMSO-$d_6$): δ1.75-2.10 (m, 8H), 2.88-3.20 (m, 8H), 3.15 (s, 2H, $CH_2CO$), 4.03-4.10 (m, 2H, $PhCH_2$), 4.98 (s, 1H), 6.80-8.10 (m, 9H, ArH), 9.6-11.0 (2B, 1H, piperidine-OH).

MS: m/z 379 (M+1)

Example 25

III-25 N-(1-(4-(1-pyrrolidinyl)phenyl)ethyl)-4-benzoylmethyl-4-piperidinol hydrochloride 4-benzoylmethyl-4-piperidinol (II) is firstly prepared according to the method of synthesis and post-treatment in General Method one. Thereafter, 2.24 g (8.8 mmol) of 1-(4-(1-bromoethyl)phenyl)pyrrolidine, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two to obtain 2.72 g of a white crystal, with yield of 70.3%.

Element analysis: $C_{25}H_{32}N_2O_2 \cdot 2HCl \cdot H_2O$ (calculated value %: C, 62.11; H, 7.51; N, 5.79; Cl, 14.67; found value %: C, 61.34; H, 7.24; N, 6.03; Cl, 15.01)

$^1$HNMR (DMSO-$d_6$): δ 1.37 (d, 3H, $CH_3$), 1.75-2.10 (m, 8H), 2.88-3.20 (m, 8H), 3.15 (s, 2H, $CH_2CO$), 4.02-4.09 (m, 1H), 4.98 (s, 1H), 6.80-8.10 (m, 9H, ArH), 9.6-11.0 (2B, 1H, piperidine-OH).

MS: m/z 393 (M+1)

Example 26

III-26 N-(4-morpholinobenzyl)-4-benzoylmethyl-4-piperidinol hydrochloride 4-benzoylmethyl-4-piperidinol (II) is firstly prepared according to the method of synthesis and post-treatment in General Method one. Thereafter, 2.25 g (8.8 mmol) of 4-morpholinobenzyl bromide, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.59 g of a white crystal, with yield of 64.3%.

Element analysis: $C_{24}H_{30}N_2O_3 \cdot 2HCl \cdot 2H_2O$ (calculated value %: C, 57.26; H, 7.21; N, 5.56; Cl, 14.08; found value %: C, 57.57; H, 7.32; N, 5.81; Cl, 14.35)

$^1$HNMR (DMSO-$d_6$): δ1.75-2.10 (m, 4H), 2.80-3.80 (m, 12H), 3.16 (s, 2H, $CH_2CO$), 4.01-4.10 (m, 2H, $PhCH_2$), 4.98 (s, 1H), 6.80-8.10 (m, 9H, ArH), 9.6-11.0 (2B, 1H, piperidine-OH).

MS: m/z 395 (M+1)

Example 27

III-27 N-(1-(4-morpholinophenyl)ethyl)-4-benzoylmethyl-4-piperidinol hydrochloride 4-benzoylmethyl-4-piperidinol (II) is firstly prepared according to the method of synthesis and post-treatment in General Method one. Thereafter, 2.38 g (8.8 mmol) of 1-bromoethyl-4-morpholinobenzene, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.50 g of a white crystal, with yield of 60.4%.

Element analysis: $C_{25}H_{32}N_2O_3 \cdot 2HCl \cdot 2H_2O$ (calculated value %: C, 58.02; H, 7.40; N, 5.41; Cl, 13.70; found value %: C, 59.27; H, 7.55; N, 5.67; Cl, 14.01)

$^1$HNMR (DMSO-$d_6$): δ 1.37 (d, 3H, $CH_3$), 1.76-2.10 (m, 4H), 2.80-3.90 (m, 12H), 3.15 (s, 2H, $CH_2CO$), 4.02-4.09 (m, 1H), 5.02 (s, 1H), 6.80-8.10 (m, 9H, ArH), 9.6-11.0 (2B, 1H, piperidine-OH).

MS: m/z 409 (M+1)

Example 28

III-28 N-(4-(1-piperidinyl)benzyl)-4-benzoylmethyl-4-piperidinol hydrochloride 4-benzoylmethyl-4-piperidinol (II) is firstly prepared according to the method of synthesis and post-treatment in General Method one. Thereafter, 2.24 g (8.8 mmol) of 4-(1-piperidinyl)benzyl bromide, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.86 g of a white crystal, with yield of 73.9%.

Element analysis: $C_{25}H_{32}N_2O_2 \cdot 2HCl \cdot H_2O$ (calculated value %: C, 62.11; H, 7.51; N, 5.79; Cl, 14.67; found value %: C, 62.28; H, 7.76; N, 6.07; Cl, 14.84)

$^1$HNMR (DMSO-$d_6$): δ1.55-2.10 (m, 10H), 2.90-3.20 (m, 8H), 3.15 (s, 2H, $CH_2CO$), 4.03-4.10 (m, 2H, $PhCH_2$), 5.01 (1B, 1H), 6.80-8.10 (m, 9H, ArH), 9.6-11.0 (2B, 1H, piperidine-OH).

MS: m/z 393 (M+1)

Example 29

III-29 N-(2-oxo-5-indolinyl)methyl-4-benzoylmethyl-4-piperidinol hydrochloride 4-benzoylmethyl-4-piperidinol (II) is firstly prepared according to the method of synthesis and post-treatment in General Method one. Thereafter, 2.00 g (8.8 mmol) of 5-bromomethyl-2-oxoindoline, 1.75 g (8.0 mmol) of 4-benzoylmethyl-4-piperidinol (II), 0.03 g (0.2 mmol) of potassium iodide and 3.53 g (25.6 mmol) of anhydrous $K_2CO_3$ is placed in anhydrous acetone (60 ml), and reacting at reflux for 12 hours. Operating according to the post-treatment procedure in General Method two obtains 2.86 g of a white crystal, with yield of 73.9%.

Element analysis: $C_{22}H_{24}N_2O_3 \cdot HCl \cdot H_2O$ (calculated value %: C, 63.08; H, 6.50; N, 6.69; Cl, 8.46; found value %: C, 63.25; H, 6.86; N, 6.47; Cl, 8.77)

$^1$HNMR (DMSO-$d_6$): δ1.80-2.10 (m, 4H, piperidine-H), 3.00-3.20 (m, 4H), 3.13 (s, 2H, $CH_2CO$), 3.49 (s, 2H), 4.02-4.08 (m, 2H), 5.01 (s, 1H, piperidine-N.HCl), 6.90-8.10 (m, 8H, ArH), 9.5-11.8 (3B, 2H).

MS: m/z 365 (M+1)

Example 30

III-30 N-(5-indolinyl)methyl-4-benzoylmethyl-4-piperidinol hydrochloride 4-benzoylmethyl-4-piperidinol (II) is firstly prepared according to the method of synthesis and post-treatment in General Method one. Thereafter, 1.87 g (8.8 mmol) of 5-bromomethylindoline, 1.75 g (8.0 mmol) of 4-benzoylmethyl-4-piperidinol (II) and 3.53 g (25.6 mmol) of anhydrous $K_2CO_3$ is placed in anhydrous acetone (60 ml), and reacting at reflux for 12 hours. Operating according to the post-treatment procedure in General Method two obtains 1.29 g of a white crystal, with yield of 36.5%.

Element analysis: $C_{22}H_{26}N_2O_2 \cdot 2HCl \cdot H_2O$ (calculated value %: C, 59.86; H, 6.85; N, 6.35; Cl, 16.06; found value %: C, 59.55; H, 6.96; N, 6.45; Cl, 16.03)

$^1$HNMR (DMSO-$d_6$): δ1.80-2.10 (m, 4H, piperidine-H), 2.80-3.20 (m, 6H), 3.15 (s, 2H, $CH_2CO$), 3.40-3.50 (m, 2H), 4.02-4.15 (m, 3H), 5.03 (s, 1H, piperidine-N.HCl), 6.90-8.10 (m, 8H, ArH), 9.5-11.0 (2B, 1H, piperidine-OH).

MS: m/z 351 (M+1)

Example 31

III-31 N-benzyl-4-(p-fluorobenzoylmethyl)-4-piperidinyl hydrobromide

Anhydrous cerium chloride (0.99 g, 4.0 mmol) and sodium iodide (1.8 g, 12.0 mmol) are added to 10 ml of anhydrous tetrahydrofuran as a solvent to form a suspension. Dissolving 0.87 g (4.0 mmol) of 2-bromo-1-(4-fluorophenyl)-ethanone and 0.76 g (4.0 mmol) of N-benzyl-4-piperidone in 10 ml of anhydrous tetrahydrofuran, and the solution is added dropwise to the above suspension and reacting at room temperature for 2 hours. Operating according to the post-treatment procedure in General Method three, and a salt is formed by acidifying with hydrobromic acid/ethanol solution, which is recrystallized in ethyl acetate/ethanol to obtain 0.58 g of a white crystal, with yield of 34.0%.

Element analysis: $C_{20}H_{22}FNO_2 \cdot HBr \cdot H_2O$ (calculated value %: C, 56.35; H, 5.91; N, 3.29; Br, 18.74; found value %: C, 56.62; H, 5.83; N, 3.46; Br, 18.57)

$^1$HNMR (DMSO-$d_6$): δ1.80-2.10 (m, 4H, piperidine-H), 3.00-3.20 (m, 4H, piperidine-H), 3.14 (s, 2H, $CH_2CO$), 4.10 (s, 2H, $PhCH_2$), 4.92 (s, 1H, piperidine-N.HBr), 7.20-8.10 (m, 9H, ArH), 9.6-11.2 (2B, 1H, piperidine-OH).

MS: m/z 328 (M+1)

Example 32

III-32 N-benzyl-4-(p-methoxybenzoylmethyl)-4-piperidinol hydrobromide

Anhydrous cerium chloride (0.99 g, 4.0 mmol) and sodium iodide (1.8 g, 12.0 mmol) are added to 10 ml of anhydrous tetrahydrofuran as a solvent to form a suspension. Dissolving 0.92 g (4.0 mmol) of 2-bromo-1-(4-methoxyphenyl)-ethanone and 0.76 g (4.0 mmol) of N-benzyl-4-piperidone in 10 ml of anhydrous tetrahydrofuran, and the solution is added dropwise to the above suspension and reacting at room temperature for 2 hours. Operating according to the post-treatment procedure in General Method three, and a salt is formed by acidifying with hydrobromic acid/ethanol solution, which is recrystallized in ethyl acetate/ethanol to obtain 0.61 g of a white crystal, with yield of 34.9%.

Element analysis: $C_{21}H_{25}NO_3 \cdot HBr \cdot H_2O$ (calculated value %: C, 57.54; H, 6.44; N, 3.20; Br, 18.23; found value %: C, 57.33; H, 6.53; N, 3.39; Cl, 18.41)

$^1$HNMR (DMSO-$d_6$): δ1.80-2.10 (m, 4H, piperidine-H), 3.00-3.20 (m, 4H, piperidine-H), 3.14 (s, 2H, $CH_2CO$), 3.94 (s, 3H), 4.05 (s, 2H, $PhCH_2$), 4.92 (s, 1H, piperidine-N.HBr), 7.20-8.10 (m, 9H, ArH), 9.6-11.0 (2B, 1H, piperidine-OH).

MS: m/z 340 (M+1)

Example 33

III-33 N-benzyl-4-(p-chlorobenzoylmethyl)-4-piperidinol hydrobromide

Anhydrous cerium chloride (0.99 g, 4.0 mmol) and sodium iodide (1.8 g, 12.0 mmol) are added to 10 ml of anhydrous tetrahydrofuran as a solvent to form a suspension. Dissolving 0.98 g (4.0 mmol) of 2-bromo-1-(4-chlorophenyl)ethanone and 0.76 g (4.0 mmol) of N-benzyl-4-piperidone in 10 ml of anhydrous tetrahydrofuran, and the solution is added dropwise to the above suspension and reacting at room temperature for 2 hours. Operating according to the post-treatment procedure in General Method three, and a salt is formed by acidifying with hydrobromic acid/ethanol solution, which is recrystallized in ethanol to obtain 0.65 g of a white crystal, with yield of 36.7%.

Element analysis: $C_{20}H_{22}ClNO_2 \cdot HBr \cdot H_2O$ (calculated value %: C, 54.25; H, 5.69; N, 6.18; Cl, 8.01; Br, 18.05; found value %: C, 54.27; H, 5.77; N, 6.37; Cl, 8.13; Br, 18.26)

$^1$HNMR (DMSO-$d_6$): δ1.80-2.10 (m, 4H, piperidine-H), 3.00-3.20 (m, 4H, piperidine-H), 3.15 (s, 2H, $CH_2CO$), 4.08 (s, 2H, $PhCH_2$), 4.92 (s, 1H, piperidine-N.HBr), 7.20-8.10 (m, 9H, ArH), 9.8-11.0 (2B, 1H, piperidine-OH).

MS: m/z 344 (M+1)

Example 34

III-34 N-benzyl-4-(2-pyridinylformylmethyl)-4-piperidinol hydrobromide

Anhydrous cerium chloride (0.99 g, 4.0 mmol) and sodium iodide (1.8 g, 12.0 mmol) are added to 10 ml of anhydrous tetrahydrofuran as a solvent to form a suspension. Dissolving 0.80 g (4.0 mmol) of 2-bromo-1-(2-pyridyl)-ethanone and 0.76 g (4.0 mmol) of N-benzyl-4-piperidone into 10 ml of anhydrous tetrahydrofuran, and the solution is added dropwise to the above suspension and reacting at room temperature for 2 hours. Operating according to the post-treatment procedure in General Method three to obtain 0.53 g of a white crystal, with yield of 36.3%.

Element analysis: $C_{19}H_{22}N_2O_2 \cdot HBr \cdot H_2O$ (calculated value %: C, 55.75; H, 6.16; N, 6.84; Br, 19.52; found value %: C, 55.81; H, 6.32; N, 6.57; Br, 19.801)

$^1$HNMR (DMSO-$d_6$): δ1.80-2.10 (m, 4H, piperidine-H), 3.00-3.20 (m, 4H, piperidine-H), 3.17 (s, 2H, $CH_2CO$), 4.01 (s, 2H), 4.91 (s, H, piperidine-N.HBr), 7.20-8.60 (m, 9H), 9.6-11.0 (2B, 1H, piperidine-OH).

MS: m/z 311 (M+1)

Example 35

III-35 N-benzyl-4-(4-(pyrrolidinyl)benzoylmethyl)-4-piperidinol hydrochloride Anhydrous cerium chloride (0.99 g, 4.0 mmol) and sodium iodide (1.8 g, 12.0 mmol) are added to 10 ml of anhydrous tetrahydrofuran as a solvent to form a suspension. Dissolving 1.07 g (4.0 mmol) of 2-bromo-1-(4-(pyrrolidin-1-yl)phenyl)ethanone and 0.76 g (4.0 mmol) of N-benzyl-4-piperidone into 10 ml of anhydrous tetrahydrofuran, and the solution is added dropwise to the above suspension and reacting at room temperature for 2 hours. Operating according to the post-treatment procedure in General Method three to obtain 0.65 g of a white crystal, with yield of 34.6%.

Element analysis: $C_{24}H_{30}N_2O_2 \cdot 2HCl \cdot H_2O$ (calculated value %: C, 61.40; H, 7.30; N, 5.97; Cl, 15.10; found value %: C, 61.56; H, 7.51; N, 6.17; Cl, 15.32)

$^1$HNMR (DMSO-$d_6$): δ1.65-2.10 (m, 8H), 2.85-3.20 (m, 8H), 3.15 (s, 2H, $CH_2CO$), 4.03 (s, 2H, $PhCH_2$), 4.98 (s, 1H), 6.80-8.10 (m, 9H, ArH), 9.6-11.0 (2B, 1H, piperidine-OH).

MS: m/z 379 (M+1)

Example 36

III-36 N-benzyl-4-((4-morpholinobenzoyl)methyl)-4-piperidinol hydrochloride

Anhydrous cerium chloride (0.99 g, 4.0 mmol) and sodium iodide (1.8 g, 12.0 mmol) are added to 10 ml of anhydrous tetrahydrofuran as a solvent to form a suspension. Dissolving 1.07 g (4.0 mmol) of 2-bromo-1-(4-morpholinophenyl)ethanone and 0.76 g (4.0 mmol) of N-benzyl-4-piperidone into 10 ml of anhydrous tetrahydrofuran, and the solution is added dropwise to the above suspension and reacting at room temperature for 2 hours. Operating according to the post-treatment procedure in General Method three to obtain 0.69 g of a white crystal, with yield of 34.3%.

Element analysis: $C_{24}H_{30}N_2O_3 \cdot 2HCl \cdot 2H_2O$ (calculated value %: C, 57.26; H, 7.21; N, 5.56; Cl, 14.08; found value %: C, 57.46; H, 7.38; N, 5.77; Cl, 14.26)

$^1$HNMR (DMSO-$d_6$): δ1.70-2.10 (m, 4H), 2.80-3.80 (m, 12H), 3.16 (s, 2H, $CH_2CO$), 4.02 (s, 2H, $PhCH_2$), 4.99 (s, 1H), 6.80-8.10 (m, 9H, ArH), 9.6-11.0 (2B, 1H, piperidine-OH).

MS: m/z 395 (M+1)

Example 37

III-37 N-benzyl-4-(2-(5-indolinyl)-2-oxoethyl)-4-piperidinol hydrochloride

Anhydrous cerium chloride (0.99 g, 4.0 mmol) and sodium iodide (1.8 g, 12.0 mmol) are added to 10 ml of anhydrous tetrahydrofuran as a solvent to form a suspension. Dissolving 0.96 g (4.0 mmol) of 2-bromo-1-(5-indolinyl)-ethanone and 0.76 g (4.0 mmol) of N-benzyl-4-piperidone into 10 ml of anhydrous tetrahydrofuran, and the solution is added dropwise to the above suspension and reacting at room temperature for 2 hours. Operating according to the post-treatment procedure in General Method three to obtain 0.64 g of a white crystal, with yield of 36.2%.

Element analysis: $C_{22}H_{26}N_2O_2 \cdot 2HCl \cdot H_2O$ (calculated value %: C, 59.86; H, 6.85; N, 6.35; Cl, 16.06; found value %: C, 59.67; H, 6.57; N, 6.19; Cl, 16.33)

$^1$HNMR (DMSO-$d_6$): δ1.80-2.10 (m, 4H, piperidine-H), 2.80-3.20 (m, 6H), 3.16 (s, 2H, $CH_2CO$), 3.40-3.50 (m, 2H), 4.03 (s, 2H), 4.98 (s, 1H, piperidine-N.HCl), 6.90-8.10 (m, 8H, ArH), 9.6-11.0 (2B, 1H, piperidine-OH).

MS: m/z 351 (M+1)

Example 38

III-38 N-benzyl-4-(2-(benzo[d][1,3]dioxol-5-yl)-2-oxoethyl)-4-piperidinol hydrochloride Anhydrous cerium chloride (0.99 g, 4.0 mmol) and sodium iodide (1.8 g of, 12.0 mmol) are added to 10 ml of anhydrous tetrahydrofuran as a solvent to form a suspension. Dissolving 0.97 g (4.0 mmol) of 1-(benzo[d][1,3]dioxol-5-yl)-2-bromo-ethanone and 0.76 g (4.0 mmol) of N-benzyl-4-piperidone into 10 ml of anhydrous tetrahydrofuran, and the solution is added dropwise to the above suspension and reacting at room temperature for 2 hours. Operating according to the post-treatment procedure in General Method three to obtain 0.70 g of a white crystal, with yield of 42.9%.

Element analysis: $C_{22}H_{26}N_2O_2 \cdot HCl \cdot H_2O$ (calculated value %: C, 61.84; H, 6.42, N, 3.43; Cl, 8.69; found value %: C, 61.57; H, 6.71; N, 3.52; Cl, 8.87)

$^1$HNMR (DMSO-$d_6$): δ1.80-2.10 (m, 4H, piperidine-H), 3.00-3.20 (m, 4H, piperidine-H), 3.13 (s, 2H, $CH_2CO$), 4.25 (s, 2H), 5.02 (s, 1H, piperidine-N.HCl), 5.92 (s, 2H), 6.90-8.10 (m, 8H, ArH), 9.6-11.0 (2B, 1H, piperidine-OH).

MS: m/z 354 (M+1)

Example 39

III-39 N-benzyl-4-(1-benzoylethyl)-4-piperidinol hydrochloride

Anhydrous cerium chloride (0.99 g, 4.0 mmol) and sodium iodide (1.8 g of, 12.0 mmol) are added to 10 ml of anhydrous tetrahydrofuran as a solvent to form a suspension. Dissolving 0.85 g (4.0 mmol) of 2-bromo-1-phenylpropanone and 0.76 g (4.0 mmol) of N-benzyl-4-piperidone into 10 ml of anhydrous tetrahydrofuran, and the solution is added dropwise to the above suspension and reacting at room temperature for 2 hours. Operating according to the post-treatment procedure in General Method three to obtain 0.46 g of a white crystal, with yield of 30.5%.

Element analysis: $C_{21}H_{25}NO_2 \cdot HCl \cdot H_2O$ (calculated value %: C, 66.74; H, 7.47; N, 3.71; Cl, 9.38; found value %: C, 66.54; H, 7.61; N, 3.94; Cl, 9.55)

$^1$HNMR (DMSO-$d_6$): δ1.37 (d, 3H), 1.80-2.10 (m, 4H, piperidine-H), 3.00-3.20 (m, 4H, piperidine-H), 3.12 (m, 1H, —CHCO), 4.11 (s, 2H), 5.01 (s, 1H, piperidine-N.HCl), 7.10-8.10 (m, 10H, ArH), 9.6-11.0 (2B, 1H, piperidine-OH).

MS: m/z 324 (M+1)

Example 40

V-1 N-p-methoxybenzyl-4-(2-hydroxy-2-phenyl-ethyl)-4-piperidinol hydrochloride

N-p-methoxybenzyl-4-benzoylmethyl-4-piperidinol(III-15) is firstly prepared according to the method of synthesis and post-treatment Example 12. Thereafter 1.36 g (4.0 mmol) of N-p-methoxybenzyl-4-benzoylmethyl-4-piperidinol is dissolved into 30 ml of an ethanol solution, and 0.17 g (4.4 mmol) of sodium borohydride is added thereto in portion, mixed and stirred at room temperature until the reaction is complete. Operating according to the post-treatment procedure in General Method four obtains 1.07 g of a white crystal, with yield of 78.4%.

Element analysis: $C_{21}H_{27}NO_3\cdot HCl\cdot H_2O$ (calculated value %: C, 63.71; H, 7.64; N, 3.54; Cl, 8.95; found value %: C, 63.54; H, 7.87; N, 3.76; Cl, 9.06)

$^1$HNMR (DMSO-$d_6$): δ1.70-2.10 (m, 6H), 3.00-3.30 (m, 5H), 3.79 (s, 3H), 4.01-4.10 (m, 2H, PhCH$_2$), 4.85-4.90 (m, 1H), 5.01 (s, 1H, piperidine-N.HCl), 7.00-8.20 (m, 9H, ArH), 11.5-12.5 (B, 1H, piperidine-OH).

MS: m/z 342 (M+1).

Example 41

V-2 N-p-acetylaminobenzyl-4-(2-hydroxy-2-phenylethyl)-4-piperidinol hydrochloride N-p-acetylaminobenzyl-4-benzoylmethyl-4-piperidinol (III-6) is firstly prepared according to the method of synthesis and post-treatment in Example 6, and 1.47 g (4.0 mmol) of N-p-acetylaminobenzyl-4-benzoylmethyl-4-piperidino is dissolved into 30 ml of an ethanol solution, and 0.17 g (4.4 mmol) of sodium borohydride is added thereto in portion, mixed and stirred at room temperature until the reaction is complete. Operating according to the post-treatment procedure in General Method four obtains 1.08 g of a white crystal, with yield of 63.9%.

Element analysis: $C_{22}H_{28}N_2O_3\cdot HCl\cdot H_2O$ (calculated value %: C, 62.48; H, 7.39; N, 6.62; Cl, 8.38; found value %: C, 62.71; H, 7.15; N, 6.94; Cl, 8.63)

$^1$HNMR (DMSO-$d_6$): δ1.70-2.10 (m, 6H), 2.02 (s, 3H), 3.00-3.30 (m, 5H), 4.01-4.10 (m, 2H, PhCH$_2$), 4.85-4.90 (m, 1H), 5.02 (s, 1H, piperidine-N.HCl), 7.00-8.20 (m, 9H, ArH), 9.80-10.2 (B, 1H), 11.5-12.5 (B, 1H, piperidine-OH).

MS: m/z 369 (M+1).

Example 42

V-3 N-diphenylmethyl-4-(2-hydroxy-2-phenylethyl)-4-piperidinol hydrochloride

N-diphenylmethyl-4-benzoylmethyl-4-piperidinol(III-7) is firstly prepared according to the method of synthesis and post-treatment in Example 7, and 1.54 g (4.0 mmol) of N-diphenylmethyl-4-benzoylmethyl-4-piperidinol is dissolved into 30 ml of an ethanol solution, and 0.17 g (4.4 mmol) of sodium borohydride is added thereto in portion, mixed and stirred at room temperature until the reaction is complete. Operating according to the post-treatment procedure in General Method four obtains 1.28 g of a white crystal, with yield of 75.5%.

Element analysis: $C_{26}H_{29}NO_2\cdot HCl$ (calculated value %: C, 73.65; H, 7.13; N, 3.30; Cl, 8.36; found value %: C, 73.51; H, 7.03; N, 3.17; Cl, 8.27)

$^1$HNMR (DMSO-$d_6$): δ1.70-2.10 (m, 6H), 3.00-3.30 (m, 5H), 4.76 (s, H, Ph$_2$CH), 4.85-4.90 (m, 1H), 5.01 (s, 1H, piperidine-N.HCl), 7.00-8.20 (m, 15H, ArH), 10.5-12.0 (B, 1H, piperidine-OH).

MS: m/z 388 (M+1).

Example 43

V-4 N-(benzo[d][1,3]dioxol-5-ylmethyl)-4-(2-hydroxy-2-phenylethyl)-4-piperidinol hydrochloride N-(benzo[d][1,3]dioxol-5-ylmethyl)-4-benzoylmethyl-4-piperidinol (III-13) is firstly prepared according to the method of synthesis and post-treatment in Example 13, and 1.41 g (4.0 mmol) of N-(benzo[d][1,3]dioxol-5-ylmethyl)-4-benzoylmethyl-4-piperidinol is dissolved into 30 ml of an ethanol solution, and 0.17 g (4.4 mmol) of sodium borohydride is added thereto in portion, mixed and stirred at room temperature until the reaction is complete. Operating according to the post-treatment procedure in General Method four obtains 1.12 g of a white crystal, with yield of 68.3%.

Element analysis: $C_{21}H_{25}NO_4\cdot HCl\cdot H_2O$ (calculated value %: C, 61.53; H, 6.89; N, 3.42; Cl, 8.65; found value %: C, 61.14; H, 7.07; N, 3.73; Cl, 8.46)

$^1$HNMR (DMSO-$d_6$): δ1.70-2.10 (m, 6H), 3.00-3.30 (m, 5H), 4.02-4.10 (m, 2H, PhCH$_2$), 4.85-4.90 (m, 1H), 5.01 (s, 1H, piperidine-N.HCl), 5.93 (s, 2H), 6.90-8.10 (m, 8H, ArH), 10.5-12.0 (B, 1H, piperidine-OH).

MS: m/z 356 (M+1).

Example 44

V-5 N-(2-methoxyphenyl)-4-(2-hydroxy-2-phenylethyl)-4-piperidinol hydrochloride

N-(2-methoxyphenyl)-4-benzoylmethyl-4-piperidinol (III-15) is firstly prepared according to the method of synthesis and post-treatment in Example 15, and 1.30 g (4.0 mmol) of N-(2-methoxyphenyl)-4-benzoylmethyl-4-piperidinol is dissolved into 30 ml of an ethanol solution, and 0.17 g (4.4 mmol) of sodium borohydride is added thereto in portion, mixed and stirred at room temperature until the reaction is complete. Operating according to the post-treatment procedure in General Method four obtains 1.06 g of a white crystal, with yield of 69.3%.

Element analysis: $C_{20}H_{25}NO_3\cdot HCl\cdot H_2O$ (calculated value %: C, 62.90; H, 7.39; N, 3.67; Cl, 9.28; found value %: C, 63.04; H, 7.57; N, 3.96; Cl, 9.60)

$^1$HNMR (DMSO-$d_6$): δ1.70-2.10 (m, 6H), 3.00-3.30 (m, 5H), 4.76 (s, 3H), 4.85-4.90 (m, 1H), 5.01 (s, 1H, piperidine-N.HCl), 6.90-8.10 (m, 9H, ArH), 10.5-12.0 (B, 1H, piperidine-OH).

MS: m/z 328 (M+1).

Example 45

V-6 N-(5-indolinyl)methyl-4-(2-hydroxy-2-phenylethyl)-4-piperidinol hydrochloride N-(5-indolinyl)methyl-4-benzoylmethyl-4-piperidinol (III-30) is prepared firstly according to the method of synthesis and post-treatment in Example 30, and 0.85 g (4.0 mmol) of N-(5-indolinyl)methyl-4-benzoylmethyl-4-piperidinol is dissolved into 30 ml of an ethanol solution, 0.17 g (4.4 mmol) of sodium borohydride is added thereto in portion, mixed and stirred at room temperature until the reaction is complete. Operating according to the post-treatment procedure in General Method four obtains 1.37 g of a white crystal, with yield of 71.8%.

Element analysis: $C_{22}H_{26}N_2O_2\cdot 2HCl\cdot 3H_2O$ (calculated value %: C, 55.35; H, 7.18; N, 5.87; Cl, 14.85; found value %: C, 55.74; H, 7.03; N, 5.56; Cl, 15.08)

$^1$HNMR (DMSO-$d_6$): δ1.70-2.10 (m, 6H), 2.80-3.30 (m, 7H), 3.40-3.50 (m, 2H), 4.02-4.15 (m, 3H), 4.85-4.90 (m, 1H), 5.01 (s, 1H, piperidine-N.HCl), 6.90-8.10 (m, 8H, ArH), 10.5-12.0 (B, 1H, piperidine-OH).

MS: m/z 353 (M+1).

Example 46

V-7 N-(1-(4-(pyrrolidinyl)phenyl)ethyl)-4-(2-hydroxy-2-phenylethyl)-4-piperidinol hydrochloride N-(4-(1-pyrrolidinyl)benzyl)-4-benzoylmethyl-4-piperidinol (III-24) is firstly prepared according to the method of synthesis and post-treatment in Example 24. 1.51 g (4.0 mmol) of N-(4-(1-pyrrolidinyl)benzyl)-4-benzoylmethyl-4-piperidinol is dissolved into 30 ml of an ethanol solution, 0.17 g (4.4 mmol) of sodium borohydride is added thereto in portion, mixed and stirred at room temperature until the reaction is complete. Operating according to the post-treatment procedure in General Method four obtains 1.31 g of a white crystal, with yield of 69.3%.

Element analysis: $C_{24}H_{32}N_2O_2 \cdot 2HCl \cdot H_2O$ (calculated value %: C, 61.14; H, 7.70; N, 5.94; Cl, 15.04; found value %: C, 61.55; H, 7.97; N, 5.76; Cl, 15.20)

$^1$HNMR (DMSO-$d_6$): δ1.37 (d, 3H, $CH_3$), 1.70-2.10 (m, 10H), 2.80-3.30 (m, 9H), 4.02-4.09 (m, 1H), 4.85-4.90 (m, 1H), 5.01 (s, 1H, piperidine-N.HCl), 6.80-8.10 (m, 9H, ArH), 10.5-12.0 (B, 1H, piperidine-OH).

MS: m/z 381 (M+1).

Example 47

V-8 N-(1-(4-morpholinophenyl)ethyl)-4-(2-hydroxy-2-phenylethyl)-4-piperidinol hydrochloride N-(1-(4-morpholinophenyl)ethyl)-4-benzoylmethyl-4-piperidinol (III-27) is firstly prepared according to the method of synthesis and post-treatment in Example 12. 1.63 g (4.0 mmol) of N-(1-(4-morpholino-phenyl)ethyl)-4-benzoylmethyl-4-piperidinol is dissolved into 30 ml of an ethanol solution, and sodium borohydride (4.4 mmol) is added thereto in portion, mixed and stirred at room temperature until the reaction is complete. Operating according to the post-treatment procedure in General Method four obtains 1.24 g of a white crystal, with yield of 62.0%.

Element analysis: $C_{25}H_{34}N_2O_3 \cdot 2HCl \cdot H_2O$ (calculated value %: C, 59.88; H, 7.64; N, 5.59; Cl, 14.14; found value %: C, 59.74; H, 7.37; N, 5.77; Cl, 14.62)

$^1$HNMR (DMSO-$d_6$): δ1.37 (d, 3H, $CH_3$), 1.70-2.10 (m, 6H), 2.80-3.30 (m, 13H), 4.01-4.10 (m, 1H), 4.85-4.90 (m, 1H), 5.01 (s, 1H, piperidine-N.HCl), 6.80-8.10 (m, 9H, ArH), 10.5-12.0 (B, 1H, piperidine-OH).

MS: m/z 411 (M+1).

Example 48

VIII-1 N-p-acetylaminobenzyl-4-benzoylmethyl-4-methoxylpiperidine hydrochloride

N-p-acetylaminobenzyl-4-benzoylmethyl-4-piperidinol (III-6) is firstly prepared according to the method of synthesis and post-treatment in Example 6. 1.47 g (4.0 mmol) of N-p-acetylaminobenzyl-4-benzoylmethyl-4-piperidinol is taken and protected on keto carbonyl according to the method in General Method five. The protected compound is dissolved into 20 ml of benzene, and 0.16 g (4.0 mmol) of 60% of NaH is added thereto slowly and stirred for 0.5 hour. The reaction solution is added dropwise a benzene solution (5.0 mmol, 5 ml) of iodomethane and stirred at room temperature until the reaction is complete. Operating according to the post-treatment and deprotection method in General Method five obtains 0.71 g of a white crystal, total yield of 40.8%.

Element analysis: $C_{23}H_{28}N_2O_3 \cdot HCl \cdot H_2O$ (calculated value %: C, 63.51; H, 7.18; N, 6.44; Cl, 8.15; found value %: C, 63.44; H, 7.43; N, 6.67; Cl, 8.47)

$^1$HNMR (DMSO-$d_6$): δ1.80-2.10 (m, 4H, piperidine-H), 2.02 (s, 3H), 3.00-3.20 (m, 4H, piperidine-H), 3.13 (s, 2H, $CH_2CO$), 3.49 (s, 3H), 4.03-4.10 (m, 2H, $PhCH_2$), 5.01 (s, 1H, piperidine-N.HCl), 7.20-8.10 (m, 9H, ArH), 9.80-10.20 (s, wide peak, 1H).

MS: m/z 381 (M+1).

Example 49

VIII-2 N-(1-(p-methoxyphenyl)ethyl)-4-benzoylmethyl-4-methoxylpiperidine hydrochloride N-(1-(4-methoxyphenyl)ethyl)-4-benzoylmethyl-4-piperidinol (III-19) is firstly prepared according to the method of synthesis and post-treatment in Example 19. 1.41 g (4.0 mmol) of N-(1-(4-methoxy phenyl)ethyl)-4-benzoylmethyl-4-piperidinol is taken and protected on keto carbonyl group according to the method in General Method five. The protected compound is dissolved into 20 ml of benzene, and 0.16 g (4.0 mmol) of 60% of NaH is added thereto slowly and stirred for 0.5 hour. The reaction solution is added dropwise a benzene solution (5.0 mmol, 5 ml) of iodomethane and stirred at room temperature until the reaction is complete. Operating according to the post-treatment and deprotection method in General Method five obtains 0.72 g of a white crystal, total yield of 42.7%.

Element analysis: $C_{23}H_{29}NO_3 \cdot HCl \cdot H_2O$ (calculated value %: C, 65.47; H, 7.64; N, 3.32; Cl, 8.40; found value %: C, 65.54; H, 7.41; N, 3.47; Cl, 8.66)

$^1$HNMR (DMSO-$d_6$): δ 1.34 (d, 3H, $CH_3$), 1.80-2.10 (m, 4H, piperidine-H), 3.00-3.20 (m, 4H, piperidine-H), 3.17 (s, 2H, $CH_2CO$), 3.45 (s, 3H), 3.82 (s, 3H), 4.03-4.10 (m, 1H), 5.01 (s, 1H), 7.00-8.10 (m, 9H, ArH).

MS: m/z 368 (M+1).

Example 50

VIII-3 N-(1-(4-morpholinophenyl)ethyl)-4-benzoylmethyl-4-methoxylpiperidine hydrochloride N-(1-(4-morpholinophenyl)ethyl)-4-benzoylmethyl-4-piperidinol (III-27) is firstly prepared according to the method of synthesis and post-treatment in Example 19. 1.63 g (4.0 mmol) of N-(1-(4-morpholinophenyl)ethyl)-4-benzoylmethyl-4-piperidinol is taken and protected on keto carbonyl according to the method in General Method five. The protected compound is dissolved into 20 ml of benzene, and 0.16 g (4.0 mmol) of 60% of NaH is added thereto slowly and stirred for 0.5 hours. The reaction solution is added dropwise a benzene solution (5.0 mmol, 5 ml) of iodomethane and stirred at room temperature until the reaction is complete. Operating according to the post-treatment and deprotection method in General Method five obtains 0.91 g of a white crystal, total yield of 44.4%.

Element analysis: $C_{26}H_{34}N_2O_3 \cdot 2HCl \cdot H_2O$ (calculated value %: C, 60.81; H, 7.46; N, 5.46; Cl, 13.81; found value %: C, 60.67; H, 7.63; N, 5.57; Cl, 14.06)

$^1$HNMR (DMSO-$d_6$): δ 1.34 (d, 3H, $CH_3$), 1.75-2.10 (m, 4H), 2.80-3.80 (m, 12H), 3.17 (s, 2H, $CH_2CO$), 3.45 (s, 3H), 4.03-4.10 (m, 1H), 5.02 (s, 1H, piperidine-N.HCl), 6.90-8.20 (m, 9H, ArH).

MS: m/z 423 (M+1).

Example 51

IX-1 N-(1-(p-methoxyphenyl)ethyl)-4-benzoylmethyl-4-fluoropiperidine hydrochloride N-(1-(4-methoxyphenyl)ethyl)-4-benzoylmethyl-4-piperidinol (III-19) is firstly prepared according to the method of synthesis and post-treatment in Example 19. 1.41 g (4.0 mmol) of N-(1-(4-methoxyphenyl)ethyl)-4-benzoylmethyl- 4-piperidinol is taken and dissolved into 20 ml of anhydrous dichloromethane and cooled with dry ice-acetone with temperature controlled at below <−70° C. The reaction solution is added dropwise a dichloromethane solution (8 mol, 25 ml) of DAST under protection of nitrogen gas. After completion of addition, the temperature is maintained at −75° C. and reacting for 1 hour, and the temperature is raised slowly and maintained at −10° C. and reacting for 2 hours. Then operating according to the post-treatment method in General Method six obtains 0.57 g of a white crystal, with yield of 34.8%.

Element analysis: $C_{22}H_{26}FNO_2 \cdot HCl \cdot H_2O$ (calculated value %: C, 64.46; H, 7.13; N, 3.42; Cl, 8.65; found value %: C, 64.74; H, 7.44; N, 3.57; Cl, 8.86)

$^1$HNMR (DMSO-$d_6$): δ 1.35 (d, 3H, $CH_3$), 1.80-2.10 (m, 4H, piperidine-H), 3.00-3.20 (m, 4H, piperidine-H), 3.16 (s, 2H, $CH_2CO$), 3.78 (s, 3H, —$OCH_3$), 4.03-4.10 (m, 1H, PhCH), 4.99 (s, 1H, piperidine-N.HCl), 7.00-8.10 (m, 9H, ArH).

MS: m/z 356 (M+1).

Example 52

IX-2 N-(benzo[d][1,3]dioxol-5-ylmethyl)-4-benzoylmethyl-4-fluoropiperidine hydrochloride N-(benzo[d][1,3]dioxol-5-ylmethyl)-4-benzoylmethyl-4-piperidinol (III-13) is firstly prepared according to the method of synthesis and post-treatment in Example 13. 1.41 g (4.0 mmol) of N-(benzo[d][1,3]dioxol-5-ylmethyl)-4-benzoylmethyl-4-piperidinol is dissolved into 20 ml of anhydrous dichloromethane and cooled with dry ice-acetone with temperature controlled at below <−70° C. The reaction solution is added a dichloromethane solution (8 mol, 25 ml) of DAST under protection of nitrogen gas. After completion of addition, the temperature is maintained at −75° C. and reacting for 1 hour, and the temperature is raised slowly and maintained at −10° C. and reacting for 2 hours. Then operating according to the post-treatment method in General Method six obtains 0.61 g of a white crystal, with yield of 37.2%.

Element analysis: $C_{21}H_{22}FNO_3 \cdot HCl \cdot H_2O$ (calculated value %: C, 64.54; H, 6.15; N, 3.42; Cl, 8.65; found value %: C, 64.69; H, 6.43; N, 3.60; Cl, 8.75)

$^1$HNMR (DMSO-$d_6$): δ 1.80-2.10 (m, 4H, piperidine-H), 3.00-3.20 (m, 4H, piperidine-H), 3.15 (s, 2H, $CH_2CO$), 4.02-4.10 (m, 2H, PhCH$_2$), 5.01 (s, 1H, piperidine-N.HCl), 5.93 (s, 2H), 7.00-8.10 (m, 8H, ArH).

MS: m/z 356 (M+1).

Example 53

IX-3 N-(1-(4-morpholinophenyl)ethyl)-4-benzoylmethyl-4-fluoropiperidine hydrochloride N-(1-(4-morpholinophenyl)ethyl)-4-benzoylmethyl-4-piperidinol (III-27) is firstly prepared according to the method of synthesis and post-treatment in Example 27. 1.63 g (4.0 mmol) of N-(1-(4-morpholino phenyl)ethyl)-4-benzoylmethyl-4-piperidinol is dissolved into 20 ml of anhydrous dichloromethane and cooled with dry ice-acetone with temperature controlled at below <−70° C. The reaction solution is added dropwise a dichloromethane solution (8 mol, 25 ml) of DAST protecting of nitrogen gas. After completion of addition, the temperature is maintained at −75° C. and reacting for 1 hour, and the temperature is raised slowly and maintained at −10° C. and reacting for 2 hours. Then operating according to the post-treatment method in General Method six obtains 0.81 g of a white crystal, with yield of 40.5%.

Element analysis: $C_{25}H_{31}FN_2O_2 \cdot 2HCl \cdot H_2O$ (calculated value %: C, 59.88; H, 7.04; N, 5.59; Cl, 14.14; found value %: C, 59.67; H, 7.33; N, 5.67; Cl, 14.45)

$^1$HNMR (DMSO-$d_6$): δ 1.34 (d, 3H, $CH_3$), 1.75-2.10 (m, 4H), 2.80-3.80 (m, 12H), 3.17 (s, 2H, $CH_2CO$), 4.03-4.10 (m, 1H), 5.02 (s, 1H, piperidine-N.HCl), 6.90-8.20 (m, 9H, ArH).

MS: m/z 411 (M+1).

Example 54

IX-4 N-(1-(4-(pyrrolidinyl)phenyl)ethyl)-4-benzoylmethyl-4-fluoropiperidine hydrochloride N-(1-(4-(1-pyrrolidinyl)phenyl)ethyl)-4-benzoylmethyl-4-piperidinol (III-25) is firstly prepared according to the method of synthesis and post-treatment in Example 2. 1.57 g (4.0 mmol) of N-(1-(4-(1-pyrrolidinyl) phenyl)ethyl)-4-benzoylmethyl-4-piperidinol is dissolved into 20 ml of anhydrous dichloromethane and cooled with dry ice-acetone with temperature controlled at below <−70° C. The reaction solution is added dropwise a dichloromethane solution (8 mol, 25 ml) of DAST under protecting of nitrogen gas. After completion of addition, the temperature is maintained at −75° C. and reacting for 1 hour, and the temperature is raised slowly and maintained at −10° C. and reacting for 2 hours. Then operating according to the post-treatment method in General Method six obtains 0.78 g of a white crystal, with yield of 40.2%.

Element analysis: $C_{25}H_{31}FN_2O \cdot 2HCl \cdot H_2O$ (calculated value %: C, 61.85; H, 7.27; N, 5.77; Cl, 14.61; found value %: C, 61.77; H, 7.43; N, 5.89; Cl, 14.91)

$^1$HNMR (DMSO-$d_6$): δ 1.37 (d, 3H, $CH_3$), 1.75-2.20 (m, 8H), 2.88-3.20 (m, 8H), 3.15 (s, 2H, $CH_2CO$), 4.02-4.10 (m, 1H), 5.00 (s, 1H), 6.80-8.10 (m, 9H, ArH).

MS: m/z 395 (M+1).

Example 55

IX-5 N-(1-(p-methoxyphenyl)ethyl)-4-benzoylmethyl-4-chloropiperidine hydrochloride N-(1-(4-methoxyphenyl)ethyl)-4-benzoylmethyl-4-piperidinol (III-19) is firstly prepared according to the method of synthesis and post-treatment in Example 19. 1.41 g (4.0 mmol) of N-(1-(4-methoxyphenyl)ethyl)-4-benzoylmethyl-4-piperidinol is dissolved into 20 ml of anhydrous dichloromethane and cooled in an ice-water bath with temperature controlled at below 0° C. The reaction solution is added dropwise a dichloromethane solution (8 mol, 25 ml) of $SOCl_2$. After completion of addition, the temperature is raised slowly to room temperature and reacting for 1 hour. Then operating according to the post-treatment method in General Method seven obtains 0.68 g of white crystal, with yield of 39.9%.

Element analysis: $C_{22}H_{26}ClNO_2 \cdot HCl \cdot H_2O$ (calculated value %: C, 61.97; H, 6.86; N, 3.29; Cl, 16.63; found value %: C, 62.05; H, 7.03; N, 3.58; Cl, 16.86)

$^1$HNMR (DMSO-$d_6$): δ 1.35 (d, 3H, $CH_3$), 1.80-2.10 (m, 4H, piperidine-H), 3.00-3.20 (m, 4H, piperidine-H), 3.17 (s, 2H, $CH_2CO$), 3.79 (s, 3H, —$OCH_3$), 4.03-4.10 (m, 1H, PhCH), 4.99 (s, 1H, piperidine-N.HCl), 7.00-8.10 (m, 9H, ArH).

MS: m/z 372 (M+1).

Example 56

IX-6 N-(benzo[d][1,3]dioxol-5-ylmethyl)-4-benzoyl-methyl-4-chloropiperidine hydrochloride N-(benzo[d][1,3]dioxol-5-ylmethyl)-4-benzoylmethyl-4-piperidinol (III-13) is firstly prepared according to the method of synthesis and post-treatment in Example 13. 1.41 g (4.0 mmol) of N-(benzo[d][1,3]dioxol-5-ylmethyl)-4-benzoylmethyl-4-piperidinol is dissolved into 20 ml of anhydrous dichloromethane and cooled in an ice-water bath with temperature controlled at below 0° C. The reaction solution is added dropwise a dichloromethane solution (8 mol, 25 ml) of $SOCl_2$. After completion of addition, the temperature is raised to room temperature slowly and reacting for 1 hour. Then operating according to the post-treatment method in General Method seven obtains 0.65 g of a white crystal, with yield of 38.1%.

Element analysis: $C_{21}H_{22}ClNO_3 \cdot HCl \cdot H_2O$ (calculated value %: C, 59.16; H, 5.91; N, 3.29; Cl, 16.63; found value %: C, 59.35; H, 6.10; N, 3.55; Cl, 16.92)

$^1$HNMR (DMSO-$d_6$): δ 1.80-2.10 (m, 4H, piperidine-H), 3.00-3.20 (m, 4H, piperidine-H), 3.15 (s, 2H, $CH_2CO$), 4.02-4.10 (m, 2H, $PhCH_2$), 5.01 (s, 1H, piperidine-N.HCl), 5.93 (s, 2H), 7.00-8.10 (m, 8H, ArH).

MS: m/z 372 (M+1).

Example 57

IX-7 N-(1-(4-morpholinophenyl)ethyl)-4-benzoylmethyl-4-chloropiperidine hydrochloride N-(1-(4-morpholinophenyl)ethyl)-4-benzoylmethyl-4-piperidinol (III-27) is firstly prepared according to the method of synthesis and post-treatment in Example 27. 1.63 g (4.0 mmol) of N-(1-(4-morpholino phenyl)ethyl)-4-benzoylmethyl-4-piperidinol is dissolved into 20 ml of anhydrous dichloromethane and cooled in an ice-water bath with temperature controlled at below 0° C. The reaction solution is added dropwise a dichloromethane solution (8 mol, 25 ml) of $SOCl_2$. After completion of addition, the temperature is raised to room temperature slowly and reacting for 1 hour. Then operating according to the post-treatment method in General Method seven obtains 0.76 g of a white crystal, with yield of 36.8%.

Element analysis: $C_{25}H_{31}ClN_2O_b \cdot 2HCl \cdot H_2O$ (calculated value %: C, 57.98; H, 6.81; N, 5.41; Cl, 20.54; found value %: C, 57.75; H, 6.69; N, 5.54; Cl, 20.82)

$^1$HNMR (DMSO-$d_6$): δ 1.34 (d, 3H, $CH_3$), 1.75-2.10 (m, 4H), 2.80-3.80 (m, 12H), 3.17 (s, 2H, $CH_2CO$), 4.03-4.10 (m, 1H), 5.01 (s, 1H, piperidine-N.HCl), 6.90-8.20 (m, 9H, ArH).

MS: m/z 427 (M+1).

Example 58

Tablets

| | |
|---|---|
| The derivative of the present invention | 25 mg |
| Sucrose | 155 mg |
| Corn starch | 65 mg |
| Magnesium stearate | 5 mg |

Preparation process: an active ingredient is blended with sucrose and corn starch, and added thereto water for wetting. The mixture is stirred evenly, dried, ground, sieved, added magnesium stearate, and mixed evenly and compressed into a tablet. Each tablet is weighted 250 mg and contains 25 mg of an active ingredient.

Example 59

Injections

| | |
|---|---|
| The derivative present invention | 10 mg |
| Water for injection | 90 mg |

Preparation process: an active ingredient is dissolved into water for injection and mixed evenly. The obtained solution is packaged into an ampoule under aseptic condition with each ampoule containing an amount of 10 mg with 1 mg/ampoule of an active ingredient.

Example 60

The Compounds' In Vivo Antalgic and Sedative Effect

1. Tested Animals:
   Kunming mice, clean class KM, purchased from Shanghai SLAC LABORATORY ANIMAL CO. LTD, breeding at general environment.
2. Administrating Mode in the Test:
   The compounds are formulated to solutions of 4 mg/ml, 2 mg/ml, and 1 mg/ml with water for injection. Animals in the control group and treatment group are all administered through subcutaneous injection at neck.
3. Test Dosages:
   The treatment groups are administered with three different dosages: 10 mg/kg, 20 mg/kg, and 40 mg/kg.
4. Test Methods:
   Aspirin is used as a positive control agent and Acetic Acid Twisting Method is used for the test.
5. Specific Test Operations:
   Thirty mice, half male and half female and weighted at between 18 and 23 g, are divided in the following five groups: negative control group, positive control group, low-dosage group, medium-dosage group and high-dosage group. Specifically,

| | | |
|---|---|---|
| negative control group | physiological saline | 0.2 ml |
| positive control group | Aspirin | 0.2 mg |
| low-dosage group | 1 mg/ml of tested compounds | 0.2 ml |
| medium-dosage group | 2 mg/ml of tested compounds | 0.2 ml |
| high-dosage group | 4 mg/ml of tested compounds | 0.2 ml |

First of all, the mice in the treatment group are administrated with a solution of tested compounds (10 mg/kg, 20 mg/kg, 40 mg/kg) through subcutaneous injection at neck, the negative control group is administrated with physiological saline (20 ml/kg) orally, and the positive control group is administrated with Aspirin (20 ml/kg) orally. Each group is administrated with 10 ml/kg of 0.7% acetic acid via intraperitoneal injection (i.p.) after one hour. After 5 minutes, times of twisting response of each group of mice is recorded in 15 minutes, and twisting response inhibiting rate of each of the treatment groups is calculated according to the following equation:

Inhibiting rate %=(average twisting times of negative control group−average twisting times of treated group)/average twisting times of negative control group×100%

6. A Sedative Effect is Evaluated by Using AC Power Tube to Record Spontaneous Activity of the Mice.
7. Testing the Antalgic and Sedative Effect of the Compounds with Single Dosage (20 mg/kg), See Table 2 for Details.

TABLE 2

| | antalgic | sedative | | antalgic | sedative | | antalgic | sedative |
|---|---|---|---|---|---|---|---|---|
| III-1 | 62 | 43 | III-21 | 57 | 70.8 | V-2 | 80 | 39.6 |
| III-2 | 14 | 44 | III-22 | 43 | 73 | V-3 | 84 | 43 |
| III-3 | 76 | 35 | III-23 | 74 | 32 | V-4 | 76 | 99 |
| III-4 | 100 | 91 | III-24 | 62 | 97 | V-5 | 72 | 86 |
| III-5 | 100 | 65 | III-25 | 80 | 93 | V-6 | 69 | 51 |
| III-6 | 45 | 75 | III-26 | 64 | 65 | V-7 | 79 | 93 |
| III-7 | 45 | 60 | III-27 | 92 | 81 | V-8 | 77 | 84 |
| III-8 | 77 | 96 | III-28 | 64 | 47 | VIII-1 | 64 | 48 |
| III-9 | 57 | 74 | III-29 | 45 | 7 | VIII-2 | 76 | 0.1 |
| III-10 | 51 | 99 | III-30 | 42 | 35 | VIII-3 | 60 | 72 |
| III-11 | 44 | 0 | III-31 | 42 | 4 | IX-1 | 76 | 26 |
| III-12 | 21 | 52 | III-32 | 49 | 32 | IX-2 | 45 | 0 |
| III-13 | 37 | 66 | III-33 | 26 | 56 | IX-3 | 64 | 42 |
| III-14 | 54 | 20 | III-34 | 75 | 92 | IX-4 | 64 | 84 |
| III-15 | 96 | 54 | III-35 | 64 | 61 | IX-5 | 68 | 88 |
| III-16 | 33 | 64 | III-36 | 41 | 27 | IX-6 | 59 | 90.1 |
| III-17 | 66 | 52 | III-37 | 52 | 36 | IX-7 | 72 | 55 |
| III-18 | 84 | 20 | III-38 | 46 | 45 | | | |
| III-19 | 91 | 52 | III-39 | 56 | 32 | | | |
| III-20 | 37 | 67 | V-1 | 76 | 56 | | | |

8. Testing Results of Part of Compounds with Multiple Dosages, See Table 3 for Details.

TABLE 3

| Name of the compound | twisting response inhibiting rate (%) | | | remark |
|---|---|---|---|---|
| | 10 mg/kg | 20 mg/kg | 40 mg/kg | |
| Aspirin | — | 89.96** | — | gavage administration |
| III-1 | 73.27* | 59.41 | 91.09** | |
| III-3 | 69.44* | 77.24** | 71.46* | |
| III-4 | 100** | 100** | 100** | |
| III-5 | 100** | 100** | 100** | |
| III-7 | 25.82 | 38.03 | 44.21 | gavage administration |
| III-15 | 55.40* | 94.37** | 100** | |
| V-3 | 60.56** | 49.77* | 68.08** | gavage administration |
| VIII-1 | 35.03* | 42.11 | 57.69 | |
| IX-1 | 60.42* | 68.70* | 81.04 | |
| IX-7 | 66.05 | 60.26* | 76.39* | |

Note:
*represents $P < 0.05$,
**represents $P < 0.01$

Example 61

Measuring In Vivo an Antalgic Effect of the Compounds Through Hot Plate Method in Mice 1. Tested Animals Kunming mice, clean class KM, purchased from Shanghai SLAC LABORATORY ANIMAL CO. LTD, breeding at general environment.

2. Administrating Mode in the Test:

The compounds are formulated to solutions of 4 mg/ml, 2 mg/ml, and 1 mg/ml with water for injection. Animals in the control group and treatment group are all administered through subcutaneous injection at neck.

3. Test Dosages:

The treatment groups are administered with three different dosages: 10 mg/kg, 20 mg/kg, and 40 mg/kg.

4. Test Methods:

Morphine is used as a positive control agent and Hot Plate Method is used for the test.

5. Specific Test Operations:

Thirty to forty mice, half male and half female and weighted at between 18 and 23 g, are used. First of all, the mice are placed on a hot plate of 55.5° C. to test basic pain threshold for two to three times. Those having basic pain threshold of 5 to 30 s are selected for this test, excluding those unqualified. 30 qualified mice are selected and divided into the following five groups: negative control group, positive control group, low-dosage group, medium-dosage group and high-dosage group. Specifically,

| negative control group | directly testing basic pain threshold | |
|---|---|---|
| positive control group | 0.2 mg/ml of Morphine | 0.2 ml |
| low-dosage group | 1 mg/ml of tested compounds | 0.2 ml |
| medium-dosage group | 2 mg/ml of tested compounds | 0.2 ml |
| high-dosage group | 4 mg/ml of tested compounds | 0.2 ml |

The mice in the treatment group are administrated with a solution of tested compounds (10 mg/kg, 20 mg/kg, 40 mg/kg) through subcutaneous injection at neck, and the positive control group is administrated with Morphine (20 ml/kg) via subcutaneous injection. After 1 hour, basic pain threshold of each group of mice is measured as pain threshold after treatment. The increasing rate of pain threshold is calculated according to the following equation:

Increasing rate of pain threshold %=(pain threshold after treatment−average basic pain threshold)/ average basic pain threshold×100%

6. Testing Results of Part of the Compounds. See Table 4 for Details.

TABLE 4

| Name of compounds | Increasing rate of pain threshold (%) | | | Remark |
|---|---|---|---|---|
| | 10 mg/kg | 20 mg/kg | 40 mg/kg | |
| Morphine | — | 202.5** | — | 2 mg/kg |
| III-1 | 99.65* | 88.95 | 147.5* | |
| III-3 | 11.91 | 18.48 | 29.45 | |
| III-4 | 19.82 | 6.47 | 15.95 | |
| III-5 | 58.29 | 75.62 | 190.5* | |
| III-7 | 82.80 | 126.1* | — | gavage administration |

TABLE 4-continued

| Name of compounds | Increasing rate of pain threshold (%) | | | Remark |
|---|---|---|---|---|
| | 10 mg/kg | 20 mg/kg | 40 mg/kg | |
| III-15 | 77.69 | 117.8* | 260.0** | |
| V-3 | 64.09 | 86.80* | 135.8* | gavage administration |
| VIII-1 | 61.04 | 76.63* | 105.20* | |
| IX-1 | 86.42 | 108.6* | 156.3 | |
| IX-7 | 79.47 | 101.3* | 130.2* | |

Note:
*represents P < 0.05,
**represents P < 0.01

Example 62

Drug Dependence Test of Compound III-15

1. The Initial Study on Drug Resistance:

It is showed through Hot Plate method that the antalgic effect generated by the mice through administrating III-15 (60 mg/kg) by oral gavage does not reversed by naloxone (1 mg/kg, ip), whereas the antalgic effect generated through Morphine and Fortanodyn (hydrochloride bucinnazine, Fortanodyn) is reversed by naloxone. The mice is administrated III-15 (60 mg/kg) by oral gavage each day for consecutive eight days. Changes in pain threshold are measured using Hot Plate method 15 minutes after each administration. The pain threshold does not show weakening under conditions of consecutive administration of III-15. The antalgic effect of positive control agent Morphine (10 mg/kg, PO) reduces gradually starting from the second day of administration, showing an obvious drug resistance. It suggests that III-15 does not show drug resistance after multiple dosing.

2. The Initial Study on Drug Addiction (Naloxone Reversal Test):

Jump and Conditioned Place Preference tests in mice are used to measure respectively the physical and psychological dependence of III-15. The mice are administrated with III-15 seven times in two days with an incrementing dosage (20-120 mg/kg, PO) and are further intravenously injected with 2 mg/kg of naloxone at three hours after the last dosing. Thereafter, no jumping behavior is observed, whereas the mice in Morphine group have obvious jumping behavior. The mice administrated with 60 mg/kg of III-15 via oral gavage each day for six consecutive days do not show Conditioned Place Preference, in contrast, the mice in Morphine group show obvious Conditioned Place Preference. The result suggests that III-15 does not have addiction after multiple dosing, which is different from Morphine.

Example 63

The Initial Study on Acute Toxicity of III-15

The Bliss method is used for statistical analysis. The mice administrated with III-15 by single oral gavage show $LD_{50}$ of 452 mg/kg. The rats administrated with III-15 by single oral gavage show $LD_{50}$ of 524 mg/kg.

Example 64

Bacterial Reverse-Mutation Assay (Ames TS) of III-15

Strains: *S. typhimurium* $TA_{97}$, $TA_{98}$, $TA_{100}$ and $TA_{102}$.

Results: The assay included two parts: without $S_9$ and with $S_9$. In the systems without $S_9$ $TA_{98}$ 5000 μg/plate, and with $S_9$ $TA_{97}$ 5000 μg/plate, inhibitory effects on bacterial for the growth were seen. All other doses showed no inhibitory effect for all other bacterial strains. For all the tested doses, there was no significant increase of revertants, and Ames test of III-15 is negative.

The above result shows that III-15 has an obvious antalgic effect and a good absorption after oral administration. III-15 does not show drug resistance after multiple dosing and has very low drug dependence potential. The Ames test is negative and the therapeutic index is high. Therefore, it has the potential to be developed as a novelty non-addiction antalgic agent.

The invention claimed is:

1. A compound represented by the following formula, or a salt thereof:

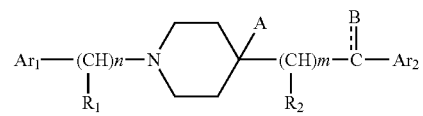

wherein:
A represents: OH, F, Cl, Br, or a $(C_1$-$C_4)$alkoxy, wherein the alkyl moiety of the $(C_1$-$C_4)$alkoxy is substituted optionally by 1-3 fluorine atom(s) and further substituted optionally by amino group or hydroxy substituent;
when B is connected with an adjacent carbon through a single bond, B represents OH;
when B is connected with an adjacent carbon through a double bond, B represents O or S;

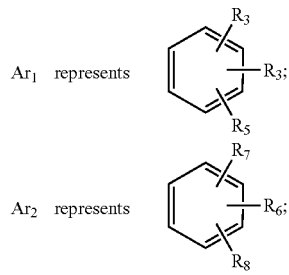

$R_1$ and $R_2$ each independently represent one selected from the group consisting of hydrogen, a $C_1$-$C_4$ alkyl, a $C_5$ or $C_6$ aliphatic ring, phenyl, substituted phenyl, hydroxy, $(C_1$-$C_4)$alkoxy, amino, substituted amino, halogen, carboxyl, carboxylic ester, nitro and acetonitrile, wherein the alkyl moiety in the $C_1$-$C_4$ alkyl, $(C_1$-$C_4)$alkoxy and $C_5$ or $C_6$ aliphatic ring is substituted optionally by 1-3 fluorine atom(s) and further substituted optionally by amino group or hydroxy group;
$R_3$, $R_4$ and $R_5$ each independently represent one selected from the group consisting of hydrogen, $C_1$-$C_4$ alkyl, a $C_5$ or $C_6$ aliphatic ring, morpholino, pyrrolidinyl, piperidinyl, phenyl, substituted phenyl, hydroxy, $(C_1$-$C_4)$ alkoxy, amino, substituted amino, halogen, carboxyl, carboxylic ester, nitro, and acetonitrile, wherein the alkyl moiety in the $C_1$-$C_4$ alkyl, ($C_1$-$C_4$)alkoxy and $C_5$ or $C_6$ aliphatic ring is substituted optionally by 1-3 fluorine atom(s) and further substituted optionally by amino group or hydroxy group;

$R_6$, $R_7$ and $R_8$ each independently represent one selected from the group consisting of hydrogen, $C_1$-$C_4$ alkyl, a $C_5$ or $C_6$ aliphatic ring, morpholino, pyrrolidinyl, piperidinyl, phenyl, substituted phenyl, hydroxy, ($C_1$-$C_4$) alkoxy, halogen, carboxyl, carboxylic ester, nitro, and acetonitrile, wherein the alkyl moiety in the $C_1$-$C_4$ alkyl, ($C_1$-$C_4$)alkoxy and $C_5$ or $C_6$ aliphatic ring is substituted optionally by 1-3 fluorine atom(s) and further substituted optionally by amino group or hydroxy group;

n=0 or 1; m=1.

2. The compound according to claim 1, wherein A is one of OH, F or Cl.

3. The compound according to claim 1, wherein $R_1$ and $R_2$ each independently represent one selected from the group consisting of hydrogen, $C_1$-$C_4$ alkyl, phenyl and substituted phenyl.

4. The compound according to claim 1, wherein $R_3$, $R_4$, and $R_5$ each independently represent one selected from the group consisting of hydrogen, $C_1$-$C_4$ alkyl, hydroxy, methoxy, ethoxy, amino, substituted amino, morpholino, pyrrolidinyl, piperidinyl, halo and nitro.

5. The compound according to claim 1, wherein $R_6$, $R_7$, and $R_8$ each independently represent one selected from the group consisting of hydrogen, $C_1$-$C_4$ alkyl, hydroxy, methoxy, ethoxy, halo, morpholino, pyrrolidinyl and piperidinyl.

6. The compound according to claim 1, wherein the salt is a hydrochloride, hydrobromide, sulfate, trifluoroacetate or methylsulfonate salt.

7. The compound according to claim 6, wherein the salt is a hydrochloride or hydrobromide salt.

8. A compound is selected from the group consisting of:
III-1 N-benzyl-4-benzoylmethyl-4-piperidinol,
III-2 N-p-chlorobenzyl-4-benzoylmethyl-4-piperidinol,
III-3 N-p-fluorobenzyl-4-benzoylmethyl-4-piperidinol,
III-4 N-p-nitrobenzyl-4-benzoylmethyl-4-piperidinol,
III-5 N-p-aminobenzyl-4-benzoylmethyl-4-piperidinol,
III-6 N-p-acetylaminobenzyl-4-benzoylmethyl-4-piperidinol,
III-7 N-diphenylmethyl-4-benzoylmethyl-4-piperidinol,
III-12 N-(2-methoxyphenyl)-4-benzoylmethyl-4-piperidinol,
III-14 N-(3,4,5-trimethoxybenzyl)-4-benzoylmethyl-4-piperidinol,
III-15 N-p-methoxybenzyl-4-benzoylmethyl-4-piperidinol,
III-16 N-(1-phenylethyl)-4-benzoylmethyl-4-piperidinol,
III-17 (R)—N-(1-phenylethyl)-4-benzoylmethyl-4-piperidinol,
III-18 (S)—N-(1-phenylethyl)-4-benzoylmethyl-4-piperidinol,
III-19 N-(1-(4-methoxyphenyl)ethyl)-4-benzoylmethyl-4-piperidinol,
III-20 N-(1-(4-fluorophenyl)ethyl)-4-benzoylmethyl-4-piperidinol,
III-21 N-(1-(4-aminophenyl)ethyl)-4-benzoylmethyl-4-piperidinol,
III-24 N-(4-(1-pyrrolidinyl)benzyl)-4-benzoylmethyl-4-piperidinol,
III-25 N-(1-(4-(1-pyrrolidinyl)phenyl)ethyl)-4-benzoylmethyl-4-piperidinol,
III-26 N-(4-morpholinobenzyl)-4-benzoylmethyl-4-piperidinol,
III-27 N-(1-(4-morpholinophenyl)ethyl)-4-benzoylmethyl-4-piperidinol,
III-28 N-(4-(1-piperidinyl)benzyl)-4-benzoylmethyl-4-piperidinol,
III-31 N-benzyl-4-(p-fluorobenzoylmethyl)-4-piperidinol,
III-32 N-benzyl-4-(p-methoxybenzoylmethyl)-4-piperidinol,
III-33 N-benzyl-4-(p-chlorobenzoylmethyl)-4-piperidinol,
III-35 N-benzyl-4-(4-(pyrrolidinyl)benzoylmethyl)-4-piperidinol,
III-36 N-benzyl-4-((4-morpholinobenzoyl)methyl)-4-piperidinol,
III-39 N-benzyl-4-(1-benzoylethyl)-4-piperidinol,
V-1 N-p-methoxybenzyl-4-(2-hydroxy-2-phenylethyl)-4-piperidinol,
V-2 N-p-acetylaminobenzyl-4-(2-hydroxy-2-phenylethyl)-4-piperidinol,
V-3 N-diphenylmethyl-4-(2-hydroxy-2-phenylethyl)-4-piperidinol,
V-5 N-(2-methoxyphenyl)-4-(2-hydroxy-2-phenylethyl)-4-piperidinol,
V-7 N-(1-(4-(pyrrolidinyl)phenyl)ethyl)-4-(2-hydroxy-2-phenylethyl)-4-piperidinol,
V-8 N-(1-(4-morpholinophenyl)ethyl)-4-(2-hydroxy-2-phenylethyl)-4-piperidinol,
VIII-1 N-p-acetylaminobenzyl-4-benzoylmethyl-4-methoxylpiperidine,
VIII-2 N-(1-(p-methoxyphenyl)ethyl)-4-benzoylmethyl-4-methoxylpiperidine,
VIII-3 N-(1-(4-morpholinophenyl)ethyl)-4-benzoylmethyl-4-methoxylpiperidine,
IX-1 N-(1-(p-methoxyphenyl)ethyl)-4-benzoylmethyl-4-fluoropiperidine,
IX-3 N-(1-(4-morpholinophenyl)ethyl)-4-benzoylmethyl-4-fluoropiperidine,
IX-4 N-(1-(4-(pyrrolidinyl)phenyl)ethyl)-4-benzoylmethyl-4-fluoropiperidine,
IX-5 N-(1-(p-methoxyphenyl)ethyl)-4-benzoylmethyl-4-chloropiperidine, and
IX-7 N-(1-(4-morpholinophenyl)ethyl)-4-benzoylmethyl-4-chloropiperidine.

9. A pharmaceutical composition comprising a therapeutically effective amount of the compound according to claim 1 and a pharmaceutically acceptable carrier.

10. A method of treating an antalgic or ataractic condition in a patient in need of the treatment, comprising administering to the patient the pharmaceutical composition of claim 9.

11. A pharmaceutical composition comprising a therapeutically effective amount of the compound according to claim 8, and a pharmaceutically acceptable carrier.

12. A method of treating an antalgic or ataractic condition in a patient in need of the treatment, comprising administering to the patient the pharmaceutical composition of claim 11.

* * * * *